(12) United States Patent
Cobbs et al.

(10) Patent No.: US 8,530,151 B2
(45) Date of Patent: Sep. 10, 2013

(54) LOCALIZATION OF HUMAN CYTOMEGALOVIRUS NUCLEIC ACIDS AND PROTEINS IN HUMAN CANCER CELLS

(75) Inventors: Charles S. Cobbs, Birmingham, AL (US); Lualhatil E. Harkins, Birmingham, AL (US)

(73) Assignees: Charles S. Cobbs, San Francisco, CA (US); Luaihati Harkins, Birmingham, AL (US)

( * ) Notice: Subject to any disclaimer, the term of this patent is extended or adjusted under 35 U.S.C. 154(b) by 1454 days.

(21) Appl. No.: 10/654,298

(22) Filed: Sep. 3, 2003

(65) Prior Publication Data

US 2004/0082005 A1    Apr. 29, 2004

Related U.S. Application Data

(60) Provisional application No. 60/407,854, filed on Sep. 3, 2002, provisional application No. 60/489,366, filed on Jul. 23, 2003.

(51) Int. Cl.
*C12Q 1/70*    (2006.01)

(52) U.S. Cl.
USPC .................................................. 435/5; 435/4

(58) Field of Classification Search
None
See application file for complete search history.

(56) References Cited

U.S. PATENT DOCUMENTS

| | | | |
|---|---|---|---|
| 4,818,678 A * | 4/1989 | Oldstone et al. | 435/5 |
| 4,839,194 A | 6/1989 | Malluche et al. | |
| 5,425,942 A | 6/1995 | Tanaka | |
| 6,162,620 A * | 12/2000 | Smith et al. | 435/69.3 |
| 6,887,464 B1 * | 5/2005 | Coleman et al. | 424/93.21 |

FOREIGN PATENT DOCUMENTS

WO    WO 97/24620 A1    7/1997

OTHER PUBLICATIONS

Muir, S.W. "Detection of cytomegalovirus in upper gastrointestinal biopsies from heart transplant recipients: comparison of light microscopy, immunocytochemistry, in situ hybridization, and nested PCR" J Clin Pathol (1998) 51: 807-811.*
Baker-Cairns et al. Biotechniques. Apr. 1996;20(4):641-50.*
Kurata et al. Ann N Y Acad Sci. 1983;420:192-207.*
Jiwa et al. J Clin Pathol. Jul. 1989;42(7):749-54.*
Grail and Norval. Gut. Oct. 1985;26(10):1053-8.*
Ramandeep et al. J Histochem Cytochem. Mar. 2001;49(3):355-68.*
Cobbs et al. Cancer Res. Jun. 15, 2002;62(12):3347-50.*
Wrensch et al. Prevalence of antibodies to four herpesviruses among adults with glioma and controls. Am J Epidemiol. Jul. 15, 2001;154(2):161-5.*
Doniger et al. Human cytomegalovirus and human herpesvirus 6 genes that transform and transactivate. Clin Microbiol Rev. Jul. 1999;12(3):367-82.*
Fish et al. Growth kinetics of human cytomegalovirus are altered in monocyte-derived macrophages. J Virol. Jun. 1995;69(6):3737-43.*
Doniger et al. 1999. Clin. Microbiol. Rev. 12:367.
Barth et al. Mem. Inst. Oswaldo. Cruz. Apr.-Jun. 1998. vol. 83, No. 2 pp. 207-212.
Kurata et al. Ann. N.Y. Acad. Sci. 1983. vol. 420, pp. 192-207.
Burd et al. Invest. Opthalmol. Vis. Sci. Sep. 1996. vol. 37, No. 10 pp. 1957-1966.
Pignatelli et al. Arch. Virol. Jun. 2002. vol. 147, No. 6 pp. 1247-1256.
Huang et al. pp. 161-193. In L.A. Philips (ed.), Viruses associated with human cancer, Marcel Dekker, Inc., New York, N.Y., 1983.
Pacsa et al. 1975. JNCI 55:775.
Boldogh et al 1983. JNCI 70:819.
Sanford et al. 1977. J. Urol. 118:789.
Hashiro et al. 1999. Intervirology 12:84-88.
Fletcher et al. 1986. Dis. Markers 4:219.
Centifanto et al. 1973. J.Virol. 12:1608.
Rapp et al. 1975. J.Virol. 16:982.
Huang et al. 1986 pp. 323-344. In C.C. Harris (ed.), Biochemical and molecular epidemiology of cancer. Alan R. Liss, Inc., New York, N.Y.
Melnick et al. 1978. Intervirology 10:115.
Stoian et al. 1982. Virologie 33:153.
Vestergaard et al. 1972. Cancer 30:68.
Fuccillo et al. 1971. Obstet. Gynecol. 38:599.
Hart et al. 1982. Gynecol. Obstet. Investig. 14:300.
Sprecher et al. 1971. Am. J. Epidememiol. 94:351.
Brichacek et al. 1980. Intervirology 14:223.
Hart et al. 1982. Gut 23:21.
Fritschy et al. 1996. J.Neurosci. 16:2275.
Poland et al. 1990. J. Infect. Dis 162:1252.
Ogura et al. 1988. J. Gen. Virol. 67:2605.
Winklhofer et al. 2000. Virology 275:323.
Del Valle et al. 2001. Cancer Res. 61:4287.
Cobbs et al. 2002. Cancer Res. 62:3351.
Dennis et al. 2002. Epidemiology 13:72.
Hayes et al. 2000 Br. J. Cancer 82:718.
Geder et al. 1977. Cancer Treat. Rep. 61:139.
Harkins et al. 2002. Lancet 360(9345):1557-63.
Goldstein et al. 1982. Infection and Immunity 38:273-281.
Jarvis et al. 1999. J.Virol 73:4552.
Tsujii et el. 1997. Pro. Natl. Acad. Sci. 94:3336.

* cited by examiner

*Primary Examiner* — Michelle S Horning
(74) *Attorney, Agent, or Firm* — Joseph R. Baker, Jr.; Gavrilovich, Dodd & Lindsey LLP

(57) ABSTRACT

The present disclosure shows human cytomegalovirus (HCMV) is strongly associated with a variety of cancers in humans. In addition, the present disclosure shows a specific strain of HCMV, HDu, is associated with several types of cancer. The identification cells harboring certain strains of HCMV, such as HDu, will provide a novel mechanism to identify cells that are at risk for undergoing oncogenesis. Novel strategies for detecting HCMV are also disclosed.

29 Claims, 11 Drawing Sheets

SEQUENCE LISTING

```
<160> NUMBER OF SEQ ID NOS: 11

<210> SEQ ID NO 1
<211> LENGTH: 258
<212> TYPE: DNA
<213> ORGANISM: Human cytomegalovirus
<220> FEATURE:
<221> NAME/KEY: misc_feature
<222> LOCATION: (1)..(2)
<223> OTHER INFORMATION: n equals any nucleic acid
<220> FEATURE:
<221> NAME/KEY: misc_feature
<222> LOCATION: (41)..(41)
<223> OTHER INFORMATION: n equals any nucleic acid
<220> FEATURE:
<221> NAME/KEY: misc_feature
<222> LOCATION: (58)..(58)
<223> OTHER INFORMATION: n equals any nucleic acid
<220> FEATURE:
<221> NAME/KEY: misc_feature
<222> LOCATION: (241)..(241)
<223> OTHER INFORMATION: n equals any nucleic acid
<220> FEATURE:
<221> NAME/KEY: misc_feature
<222> LOCATION: (243)..(257)
<223> OTHER INFORMATION: n equals any nucleic acid

<400> SEQUENCE: 1
nnctgcttct cgcaccttac aaccgtccag gcaacaacaa ntgcaacaac ttctacanca      60
actacgagga gcacgacctc atcgacaact agtactaaac tcagttccac cacccacgac     120
cctaatgtga tgagacgaca tgctaacgat gatttttaca aggcgcattg cacatcacat     180
atgtatgagc tctcactgtc cagctttgcg gcctggtgga ctatgcttaa cgctctcaaa     240
ngnnnnnnnn nnnnnnnc                                                   258

<210> SEQ ID NO 2
<211> LENGTH: 225
<212> TYPE: DNA
<213> ORGANISM: Human cytomegalovirus
<220> FEATURE:
<221> NAME/KEY: misc_feature
```

-continued

```
<222> LOCATION: (22)..(22)
<223> OTHER INFORMATION: n = any nucleic acid
<220> FEATURE:
<221> NAME/KEY: misc_feature
<222> LOCATION: (204)..(204)
<223> OTHER INFORMATION: n = any nucleic acid
<220> FEATURE:
<221> NAME/KEY: misc_feature
<222> LOCATION: (206)..(207)
<223> OTHER INFORMATION: n = any nucleic acid
<220> FEATURE:
<221> NAME/KEY: misc_feature
<222> LOCATION: (209)..(220)
<223> OTHER INFORMATION: n = any nucleic acid
<220> FEATURE:
<221> NAME/KEY: misc_feature
<222> LOCATION: (222)..(222)
<223> OTHER INFORMATION: n = any nucleic acid
<220> FEATURE:
<221> NAME/KEY: misc_feature
<222> LOCATION: (224)..(225)
<223> OTHER INFORMATION: n = any nucleic acid

<400> SEQUENCE: 2
aactgcaaca acttctactc cnactacgag gagcacgacc tcatcgacaa ctagtactaa      60
actcagttcc accacccacg acgcctaatg tgatgagacg acatgctaac gatgattttt     120
acaaggcgca ttgcacatca catatgtatg agctctcact gtccagcttt gcggcctggt     180
ggactatgct taacgctctc aaangnncnn cnnnnncnnn cngnn                     225

<210> SEQ ID NO 3
<211> LENGTH: 245
<212> TYPE: DNA
<213> ORGANISM: Human cytomegalovirus
<220> FEATURE:
<221> NAME/KEY: misc_feature
<222> LOCATION: (13)..(13)
<223> OTHER INFORMATION: n = any nucleic acid
<220> FEATURE:
<221> NAME/KEY: misc_feature
<222> LOCATION: (16)..(17)
<223> OTHER INFORMATION: n = any nucleic acid
<220> FEATURE:
<221> NAME/KEY: misc_feature
<222> LOCATION: (20)..(20)
<223> OTHER INFORMATION: n = any nucleic acid
<220> FEATURE:
<221> NAME/KEY: misc_feature
<222> LOCATION: (23)..(23)
<223> OTHER INFORMATION: n = any nucleic acid
<220> FEATURE:
<221> NAME/KEY: misc_feature
<222> LOCATION: (39)..(39)
<223> OTHER INFORMATION: n = any nucleic acid
<220> FEATURE:
<221> NAME/KEY: misc_feature
<222> LOCATION: (45)..(45)
<223> OTHER INFORMATION: n = any nucleic acid
<220> FEATURE:
<221> NAME/KEY: misc_feature
<222> LOCATION: (50)..(50)
<223> OTHER INFORMATION: n = any nucleic acid
<220> FEATURE:
<221> NAME/KEY: misc_feature
<222> LOCATION: (53)..(53)
<223> OTHER INFORMATION: n = any nucleic acid
<220> FEATURE:
<221> NAME/KEY: misc_feature
<222> LOCATION: (55)..(55)
<223> OTHER INFORMATION: n = any nucleic acid
<220> FEATURE:
<221> NAME/KEY: misc_feature
<222> LOCATION: (57)..(58)
<223> OTHER INFORMATION: n = any nucleic acid
<220> FEATURE:
<221> NAME/KEY: misc_feature
```

```
<222> LOCATION: (66)..(66)
<223> OTHER INFORMATION: n = any nucleic acid
<220> FEATURE:
<221> NAME/KEY: misc_feature
<222> LOCATION: (70)..(70)
<223> OTHER INFORMATION: n = any nucleic acid
<220> FEATURE:
<221> NAME/KEY: misc_feature
<222> LOCATION: (112)..(112)
<223> OTHER INFORMATION: n = any nucleic acid
<220> FEATURE:
<221> NAME/KEY: misc_feature
<222> LOCATION: (122)..(122)
<223> OTHER INFORMATION: n = any nucleic acid
<220> FEATURE:
<221> NAME/KEY: misc_feature
<222> LOCATION: (126)..(126)
<223> OTHER INFORMATION: n = any nucleic acid
<220> FEATURE:
<221> NAME/KEY: misc_feature
<222> LOCATION: (130)..(130)
<223> OTHER INFORMATION: n = any nucleic acid
<220> FEATURE:
<221> NAME/KEY: misc_feature
<222> LOCATION: (137)..(137)
<223> OTHER INFORMATION: n = any nucleic acid
<220> FEATURE:
<221> NAME/KEY: misc_feature
<222> LOCATION: (146)..(146)
<223> OTHER INFORMATION: n = any nucleic acid
<220> FEATURE:
<221> NAME/KEY: misc_feature
<222> LOCATION: (150)..(150)
<223> OTHER INFORMATION: n = any nucleic acid
<220> FEATURE:
<221> NAME/KEY: misc_feature
<222> LOCATION: (182)..(182)
<223> OTHER INFORMATION: n = any nucleic acid
<220> FEATURE:
<221> NAME/KEY: misc_feature
<222> LOCATION: (226)..(226)
<223> OTHER INFORMATION: n = any nucleic acid
<220> FEATURE:
<221> NAME/KEY: misc_feature
<222> LOCATION: (230)..(230)
<223> OTHER INFORMATION: n = any nucleic acid
<220> FEATURE:
<221> NAME/KEY: misc_feature
<222> LOCATION: (232)..(232)
<223> OTHER INFORMATION: n = any nucleic acid
<220> FEATURE:
<221> NAME/KEY: misc_feature
<222> LOCATION: (238)..(239)
<223> OTHER INFORMATION: n = any nucleic acid
<220> FEATURE:
<221> NAME/KEY: misc_feature
<222> LOCATION: (241)..(241)
<223> OTHER INFORMATION: n = any nucleic acid
<220> FEATURE:
<221> NAME/KEY: misc_feature
<222> LOCATION: (244)..(244)
<223> OTHER INFORMATION: n = any nucleic acid

<400> SEQUENCE: 3
agcatgtcat acnccnnctn canagggagg accgactcnc ctcanccaan tangncnnat      60
actcanagtn gcaccacgcg cactgatcgc atagactgtc gtagtgatga cnacgatcgc     120
cnaacnatgn gttttgncga ggcgcnttgn acatgcacac ttatgatatg agctctcact     180
gnacagcttt gcggcctggt ggactatgct taacgctctc aaaaangccn cnaccctnnc     240 nacnc                                                                245

<210> SEQ ID NO 4
<211> LENGTH: 254
<212> TYPE: DNA
<213> ORGANISM: Human cytomegalovirus
```

```
<220> FEATURE:
<221> NAME/KEY: misc_feature
<222> LOCATION: (1)..(2)
<223> OTHER INFORMATION: n = any nucleic acid
<220> FEATURE:
<221> NAME/KEY: misc_feature
<222> LOCATION: (7)..(7)
<223> OTHER INFORMATION: n = any nucleic acid
<220> FEATURE:
<221> NAME/KEY: misc_feature
<222> LOCATION: (55)..(55)
<223> OTHER INFORMATION: n = any nucleic acid
<220> FEATURE:
<221> NAME/KEY: misc_feature
<222> LOCATION: (237)..(241)
<223> OTHER INFORMATION: n = any nucleic acid
<220> FEATURE:
<221> NAME/KEY: misc_feature
<222> LOCATION: (245)..(253)
<223> OTHER INFORMATION: n = any nucleic acid

<400> SEQUENCE: 4
nntagcntct cgcacttaca ccgtcaaggc acaacaactg caacaacttc tacancaact    60
acgaggagca cgacctcatc gacaactagt actaaactca gttccaccac ccacgaccct   120
aatgtgatga gacgacatgc taacgatgat ttttacaagg cgcattgcac atcacatatg   180
tatgagctct cactgtccag ctttgcggcc tggtggacta tgcttaacgc tctcaannnn   240
natannnnnn nnnc                                                     254

<210> SEQ ID NO 5
<211> LENGTH: 261
<212> TYPE: DNA
<213> ORGANISM: Human cytomegalovirus
<220> FEATURE:
<221> NAME/KEY: misc_feature
<222> LOCATION: (1)..(1)
<223> OTHER INFORMATION: n = any nucleic acid
<220> FEATURE:
<221> NAME/KEY: misc_feature
<222> LOCATION: (7)..(7)
<223> OTHER INFORMATION: n = any nucleic acid
<220> FEATURE:
<221> NAME/KEY: misc_feature
<222> LOCATION: (10)..(10)
<223> OTHER INFORMATION: n = any nucleic acid
<220> FEATURE:
<221> NAME/KEY: misc_feature
<222> LOCATION: (240)..(261)
<223> OTHER INFORMATION: n = any nucleic acid

<400> SEQUENCE: 5
ntctacnatn tcgcccttac accgtgcaag gcaacaacaa ctgcaacaac ttctacaaca    60
actacgagga gcacgacctc atcgacaact agtactaaac tcagttccac cacccacgac   120
cctaatgtga tgagacgaca tgctaacgat gattttaca aggcgcattg cacatcacat    180
atgtatgagc tctcactgtc cagctttgcg gcctggtgga ctatgcttaa cgctctcaan   240
nnnnnnnnnn nnnnnnnnnn n                                             261

<210> SEQ ID NO 6
<211> LENGTH: 174
<212> TYPE: DNA
<213> ORGANISM: Human cytomegalovirus
<220> FEATURE:
<221> NAME/KEY: misc_feature
<222> LOCATION: (1)..(1)
<223> OTHER INFORMATION: n = any nucleic acid
<220> FEATURE:
<221> NAME/KEY: misc_feature
<222> LOCATION: (153)..(159)
<223> OTHER INFORMATION: n = any nucleic acid
```

```
<220> FEATURE:
<221> NAME/KEY: misc_feature
<222> LOCATION: (164)..(164)
<223> OTHER INFORMATION: n = any nucleic acid

<400> SEQUENCE: 6 ngggggctaaa ctcacgttcc accacccacg accctaatgt gatgagacga catgctaacg      60 atgatttta caaggcgcat tgcacatcac atatgtatga gctctcactg tgccagcttt      120
gcggcctggt ggactatgct taacgctctc aannnnnnnt tttntgcccc ccgc          174

<210> SEQ ID NO 7
<211> LENGTH: 234
<212> TYPE: DNA
<213> ORGANISM: Human cytomegalovirus
<220> FEATURE:
<221> NAME/KEY: misc_feature
<222> LOCATION: (2)..(2)
<223> OTHER INFORMATION: n = any nucleic acid
<220> FEATURE:
<221> NAME/KEY: misc_feature
<222> LOCATION: (17)..(17)
<223> OTHER INFORMATION: n = any nucleic acid
<220> FEATURE:
<221> NAME/KEY: misc_feature
<222> LOCATION: (217)..(225)
<223> OTHER INFORMATION: n = any nucleic acid
<220> FEATURE:
<221> NAME/KEY: misc_feature
<222> LOCATION: (228)..(228)
<223> OTHER INFORMATION: n = any nucleic acid
<220> FEATURE:
<221> NAME/KEY: misc_feature
<222> LOCATION: (231)..(231)
<223> OTHER INFORMATION: n = any nucleic acid

<400> SEQUENCE: 7
gnccaggcaa caagaanatg caacaacttc tacaccaact acgaggagca cgacctcatc      60
gacaactagt actaaactca gttccaccac ccacgaccct aatgtgatga acgacatgc      120 taacgatgat ttttacaagg cgcattgcac atcacatatg tatgagctct cactgtccag      180
ctttgcggcc tggtggacta tgcttaacgc tctcaannnn nnnnttncc nccc           234

<210> SEQ ID NO 8
<211> LENGTH: 257
<212> TYPE: DNA
<213> ORGANISM: Human cytomegalovirus
<220> FEATURE:
<221> NAME/KEY: misc_feature
<222> LOCATION: (2)..(2)
<223> OTHER INFORMATION: n = any nucleic acid
<220> FEATURE:
<221> NAME/KEY: misc_feature
<222> LOCATION: (7)..(7)
<223> OTHER INFORMATION: n = any nucleic acid
<220> FEATURE:
<221> NAME/KEY: misc_feature
<222> LOCATION: (118)..(118)
<223> OTHER INFORMATION: n = any nucleic acid
<220> FEATURE:
<221> NAME/KEY: misc_feature
<222> LOCATION: (236)..(256)
<223> OTHER INFORMATION: n = any nucleic acid

<400> SEQUENCE: 8
tnctctntcg caccttacac cgtgcaaggc aacaacaact gcaacaactt ctacaacaac      60
tacgaggagc acgacctcat cgacaactag tactaaactc agttccacca cccacgancc      120
taatgtgatg agacgacatg ctaacgatga ttttacaag gcgcattgca catcacatat      180
gtatgagctc tcactgtcca gctttgcggc ctggtggact atgcttaacg ctctcaannn      240
```
nnnnnnnnnn nnannng                                                       257

<210> SEQ ID NO 9
<211> LENGTH: 262
<212> TYPE: DNA
<213> ORGANISM: Human cytomegalovirus
<220> FEATURE:
<221> NAME/KEY: misc_feature
<222> LOCATION: (2)..(3)
<223> OTHER INFORMATION: n = any nucleic acid
<220> FEATURE:
<221> NAME/KEY: misc_feature
<222> LOCATION: (7)..(7)
<223> OTHER INFORMATION: n = any nucleic acid
<220> FEATURE:
<221> NAME/KEY: misc_feature
<222> LOCATION: (9)..(9)
<223> OTHER INFORMATION: n = any nucleic acid
<220> FEATURE:
<221> NAME/KEY: misc_feature
<222> LOCATION: (240)..(262)
<223> OTHER INFORMATION: n = any nucleic acid

<400> SEQUENCE: 9
cnntgcntnt cgcaccttac accgtgcaag gcaacaacaa ctgcaacaac ttctacaaca      60
actacgagga gcacgacctc atcgacaact agtactaaac tcagttccac cacccacgac     120
cctaatgtga tgagacgaca tgctaacgat gattttttaca aggcgcattg cacatcacat    180
atgtatgagc tctcactgtc cagctttgcg gcctggtgga ctatgcttaa cgctctcaan    240
nnnnnnnnnn nnnnnnnnnn nn                                              262

<210> SEQ ID NO 10
<211> LENGTH: 243
<212> TYPE: DNA
<213> ORGANISM: Human cytomegalovirus
<220> FEATURE:
<221> NAME/KEY: misc_feature
<222> LOCATION: (54)..(54)
<223> OTHER INFORMATION: n = any nucleic acid
<220> FEATURE:
<221> NAME/KEY: misc_feature
<222> LOCATION: (223)..(223)
<223> OTHER INFORMATION: n = any nucleic acid
<220> FEATURE:
<221> NAME/KEY: misc_feature
<222> LOCATION: (231)..(231)
<223> OTHER INFORMATION: n = any nucleic acid
<220> FEATURE:
<221> NAME/KEY: misc_feature
<222> LOCATION: (234)..(235)
<223> OTHER INFORMATION: n = any nucleic acid
<220> FEATURE:
<221> NAME/KEY: misc_feature
<222> LOCATION: (237)..(237)
<223> OTHER INFORMATION: n = any nucleic acid

<400> SEQUENCE: 10
caccgcctca ggcaacaaga aaatgcaaca acttctactc caactacgag gagnacgacc     60
tcatcgacaa ctagtactaa actcagttcc accacccacg acctaatgt gatgagacga     120 catgctaacg atgattttta caaggcgcat tgcacatcac atatgtatga gctctcactg    180
tccagctttg cggcctggtg gactatgctt aacgctctca aangaccatc nagnncngcc    240
tgg                                                                   243

<210> SEQ ID NO 11
<211> LENGTH: 21
<212> TYPE: DNA
<213> ORGANISM: artificial sequence -continued

```
<220> FEATURE:
<223> OTHER INFORMATION: probe

<400> SEQUENCE: 11
gtggtggcgc tggggtggc g                                               21
```

LOCALIZATION OF HUMAN CYTOMEGALOVIRUS NUCLEIC ACIDS AND PROTEINS IN HUMAN CANCER CELLS

FIELD OF DISCLOSURE

This application claims priority to and the benefit of U.S. provisional patent application No. 60/407,854, filed Sep. 3, 2002, and U.S. provisional patent application No. 60/489,366, filed Jul. 23, 2003. The following disclosure relates to the field of virology, specifically human cytomegalovirus (HCMV).

BACKGROUND

The human herpesviruses are grouped into three subfamilies: 1) the Alphaherpesvirinae, which includes human simplex virus 1 (HSV-1), human simplex virus 2 (HSV-2), and varicella-zoster virus; 2) the Betaherpesvirinae, which includes human cytomegalovirus (HCMV) human herpesvirus 6 (HHV-6), human herpesvirus 7 (HHV-7); and 3) the Gammaherpesvirinae, which includes Epstein-Barr virus (EBV) and human herpesvirus 8 (HHV-8) (Roizman, B. 1996. Herpesviridae, p. 2221-2230. In B. N. Fields, D. M. Knipe, and P. M. Howley (ed.), Virology. Lippincott-Raven, Philadelphia, Pa.). Although the human herpesviruses generally cause asymptomatic infections in immuno-competent individuals, these viruses can cause severe, life-threatening infections in immuno-compromised individuals. In general, these viruses can be reactivated following primary exposure.

Members of the herpesvirus family have been implicated in the etiology of several human cancers. For example, EBV, HSV-2, HHV-6, HHV-8, and HCMV have been associated with cancers in a wide range of organ systems (Reviewed in Doniger et al., 1999. Clin. Microbiol. Rev. 12:367). However, the exact role of the herpesvirus family in cancer etiology is unknown and the data have failed to establish a causative link between specific disease states and individual viruses.

HCMV is endemic to the human population and persistently infects 70-95% of the US adult population. In healthy, immuno-competent adults, most HCMV infections are asymptomatic. In addition, about 0.5 to 2.5% of all newborns are infected at birth, with a majority of these infections being asymptomatic. However, in immuno-compromised individuals, HCMV can cause severe disseminated disease characterized by chorioretinitis, pneumonia, esophagitis, colitis, myelitis, meningitis, encephalitis, leukopenia, lymphocytosis, and hepatitis. HCMV infections can be reactivated following latentcy following blood transfusions, pregnancy, solid-organ or bone marrow transplantation, immunosuppressive therapy, or other viral infections. HCMV infects a wide range of cell types, including leukocytes, endothelial cells, connective tissue cells, and epithelial cells (Hirsch, M. S. 1984. Ser. 20:161; Myerson et al.1984. Hum. Pathol. 15:431; Rapp, F. 1984. JNCI 72:783). HCMV is transmitted through milk, semen, urine, saliva, and cervical secretions and may be acquired via the transplacental, perinatal, and sexual routes, through blood transfusion and organ or bone marrow transplantation.

A definitive role of HCMV in human cancer has not been established. The ubiquitous distribution of HCMV in the human population and the high seroconversion rates of HCMV make establishing a clear etiological association difficult. Furthermore, the large size of HCMV (230 kbp) makes the detection of small viral DNA sequences (1,000 bp) associated with the initiation or progression of cancer very difficult when a whole genomic probe is used.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In FIG. 4A, multiple electron dense particles ranging from 150-250 nm are observed (arrows) in a cell surrounded by myelinated axons (open arrows) at 8,000×(bar, 1 μm).

DETAILED DESCRIPTION

Figure 1:
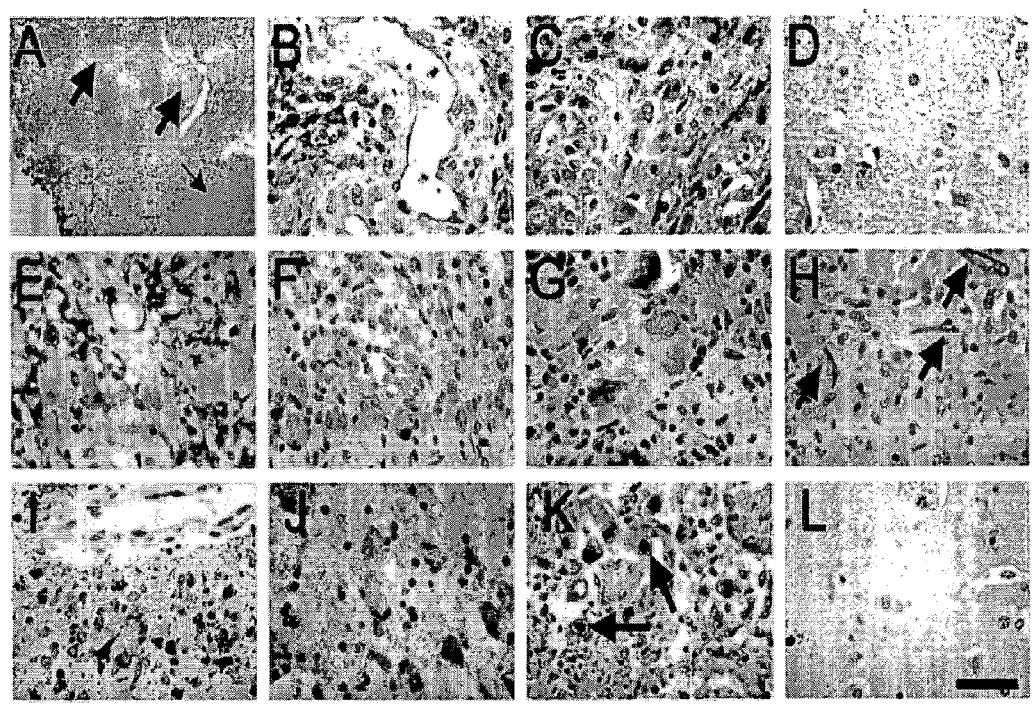
FIG. 1 shows immunohistochemical localization of HCMV proteins in human gliomas. Anti-IE1-72 immunoreactivity in 4 representative GBMs (A-C & F), a grade II astrocytoma (D) and a grade III oligoastrocytoma (E) (chromogen DAB, brown). Anti-IE1-72 (G), anti-p52/anti-76 kD (H), and anti-pp65 (I) immunoreactivity is seen in different sections from the same GBM. A giant tumor cell shows nuclear and cytoplasmic pp65 immunoreactivity (I). Anti-IE1-72 immunoreactivity is absent in normal brain (J). Isotype control anti-CD34 antibody reacts with blood vessels (arrows) in normal (K) specimens, but not tumor cells (L). Bar, 10 μm.

HCMV has been associated with cervical carcinoma (Huang et al. p. 161-193. In L. A. Philips (ed.), Viruses associated with human cancer. Marcel Dekker, Inc., New York, N.Y.; Pacsa et al. 1975. JNCI. 55:775), adenocarcinomas of the prostate (Boldogh et al., 1983. JNCI 70:819; Sanford et al. 1977. J. Urol. 118:789) and colon (Hashiro et al. 1999. Intervirology 12:84; Huang et al. 1978. Lancet i:957), and Kaposi's sarcoma (KS) (Boldogh et al. 1981. Int. J. Cancer 28:469; Giraldo et al. 1978. Int. J. Cancer 22:126; Giraldo et al. 1980. Int. J. Cancer 26:23).

Several investigators have detected HCMV DNA in cervical cancer specimens (Huang et al. 1983; Fletcher et al. 1986 Dis. Markers 4:219). However, DNAs of several other viruses, including HSV-2 and human papillomavirus (HPV), have also been detected in these tumors (McDougall et al. 1984. J. Investig. Dermatol. 83:72s) raising the possibility possible that synergistic interactions among these viruses in the infected cell leads to the development of cervical cancer. Furthermore, HCMV nuclear antigens and DNA have been detected in prostatic carcinoma cells (Centifanto et al. 1973 J. Virol.12:1608), and one HCMV strain, Mj, has been isolated from a primary culture of human prostatic tissue (Rapp et al. 1978 J. Virol. 16:982). HCMV has also been isolated from cell cultures derived from adenocarcinomas of the colon (Hashiro et al. 1979 Intervirology 12:84-88).

The findings, however, are often contradictory making a precise determination of HCMV in carcinogenesis difficult. For example, in cervical cancer, HCMV has been isolated from cancer biopsy specimens and their derived cell cultures (Huang et al. 1986. p. 323-344. In C. C. Harris (ed.), Biochemical and molecular epidemiology of cancer. Alan R. Liss, Inc., New York, N.Y.; Melnick et al. 1978. Intervirology 10:115). However, seroepidemiologic studies linking HCMV infection to cervical cancer have yielded conflicting results, with some studies reporting higher levels of antibodies to HCMV in patients with cervical carcinoma than in controls (.Pacsa et al. 1975. JNCI. 55:775; Stoian et al. 1982. Virologie 33:153; Vestergaard et al. 1972. Cancer 30:68), and other studies reporting no correlation (Fuccillo et al. 1971. Obstet. Gynecol. 38:599; Hart et al. 1982 Gynecol. Obstet. Investig. 14:300; Sprecher et al.1971. Am. J. Epidemiol. 94:351). In the gastrointestinal tract, HCMV DNA was detected in adenocarcinomas of the colon in one study (Huang et al. 1978). However, other studies reported no HCMV DNA sequences in tumor biopsy specimens from adenocarcinomas of the colon and rectum (Brichacek et al. 1980. Intervirology 14:223: Hart et al. 1982 Gut 23:21).

HCMV has also been shown to transform a range of cells in vitro. Both infective and UV-inactivated virus particles have been shown to transform cells. UV-inactivated HCMV was shown to transform hamster embryo fibroblasts, with the transformed cells inducing poorly differentiated malignant fibrosarcomas after subcutaneous injection into newborn and weanling golden Syrian hamsters. Interestingly, no HCMV DNA was detected in the transformed cells, although HCMV-specific antigens were demonstrated in the transformed and tumor-derived lines (Albrecht et al. 1973. Virology 55:53; Boldogh et al. 1978 Microbiol. Acad. Sci. Hung. 25:269). HCMV is also capable of transforming human cell lines in vitro. HCMV strain Mj (Geder et al. 1976. Science192:1134), BT1757 (Huang et al. 1986 p. 323-344. In C. C. Harris (ed.), Biochemical and molecular epidemiology of cancer. Alan R. Liss, Inc., New York, N.Y.), or Towne (Huang et al. 1986) transformed human embryo lung cells. The transformed cells exhibited enhanced tumorigenicity in nude mice (Geder et al. 1978. IARC Sci. Publ. 24:591). Human endothelial cells were also transformed to anchorage-independent growth by infection with strains Towne and K9V (Smiley et al. 1988. J. Med. Virol. 25:215).

A growing body of evidence indicates that HCMV possesses multiple oncogenic properties and that HCVM gene expression can promote mutagenesis, cell cycle progression, angiogenesis, cell invasion and immune evasion (Doniger, et al.1999; Shen et al. 1997. Proc. Natl. Acad. Sci. USA 94:3341; Zhu, et al 1995 Virol. 69:7960; Bresnahan et al. 1998 J. Biol. Chem. 273:22075; Scholz et al. 2000 Tissue Antigens 55:412; Speir et al. 1994 Science 265:391). The HCMV immediate early proteins (IE1 and IE2) are highly mutagenic, are anti-apoptotic, and can interact with and disable the p53 and Rb family of tumor suppressor proteins (Zhu et al 1995; Shen et al. 1997). HCMV infection induces high levels of cyclooxygenase-2 (COX-2) expression, and inhibits thrombospondin-1 (TSP-1) expression, both of which can contribute to angiogenesis (Zhu et al. 1998 PNAS 95:14470; Cinatl et al. 1999 Am. J Pathol. 155:285). HCMV can induce sustained c-myc, p38 MAPK and Bcl-2 expression, which can induce cell de-differentiation, proliferation and insensitivity to apoptotic signals (Hagemeier et al. 1992. J. Gen. Virol. 73:2385). HCMV-infected tumor cells display increased extracellular matrix invasiveness that is associated with alterations in integrin expression (Scholz et al. 2000). HCMV infection has also been shown to induce cell cycle arrest at the G2/M boundary (Jault et al. 1995. J. Virol. 69:6697) and to stimulate cell cycle progression from G0 into the G1 and S phases (Bresnahan et al. 1998; Bresnahan et al. 1997 J. Gen. Virol. 78:1993). In addition to dysregulating multiple oncogenic pathways, HCMV can severely impair host immune responses to infected cells by disabling multiple proteins involved in MHC Class I and II and NK cell immune recognition. Recent data also indicate that the cell type involved in HCMV infection can profoundly impact viral replication, gene expression and protein trafficking. In the case of human epithelial cells (caco-2 cells), HCMV infection can only occur when these cells are in an early state of differentiation, and in these cells productive infection is rare and virus does not spread from cell to cell.

Several morphological transforming regions (mtr) have been identified in HCMV. These include mtr I, mtr II and mtr III (reviewed in Doniger et al. 1999). These mtr sequences have been shown to transform cell in vitro, and to induce tumors in animal models. mtr I and III sequences are typically not detected in transformed cells, suggesting that these sequences may contribute to cellular transformation, but are not required for the maintenance of the transformed phenotype. This has led to the "hit and run" mechanisms for cellular transformation by HCMV. mtr II sequences are retained in transformed cells, suggesting that mtr II sequences are required for the maintenance of the transformed phenotype.

Furthermore, clinical isolates of HCMV show differences in tissue tropism, the ability to establish latent versus active infections and the severity of infection (Pignatelli et al. 2001. J. Gen. Virol. 82:2777-2784). These differences are postulated to be caused by genomic variations between HCMV strains, causing differences in polypeptide structure and/or function. The sequence similarity between different HCMV strains varies greatly depending on the genomic region analyzed. There have been several highly variable regions identified in the HCMV genome. These variable genomic variants include the genes coding for UL4, UL144, gH, gB and gN. These hypervariable regions may be responsible for cell specificity and specific immune responses. gN is coded by ORF UL73 (the UL73 sequences of 38 clinical strains have been assigned GenBank accession nos. AF309969 through AF310006, such sequences being incorporated by reference herein). Significantly, gN shows a high degree of sequence variability between HCMV strains, a feature not seen in other herpesviruses (Dal Monte et al., 2001. J. Hum. Virol. 4:26-34).

The present disclosure shows that HCMV infection is strongly associated with several types of cancers in humans, including glioma, prostate and colorectal cancer. In addition, the present disclosure shows a specific strain of HCMV, HDu, is associated with such cancers. The tissue specificity of HCMV may be mediated by glycoprotein N (UL73, gN) of the HDu strain. Therefore, the identification of cells harboring strains of HCMV, or specific strains of HCMV such as HDu, will provide a novel mechanism to identify cells that are at risk for undergoing oncogenesis. In addition, gN is contemplated for use in the development of a strain specific humoral and/or cell mediated immune response capable of blocking and/or reducing HCMV mediated oncogenesis. Furthermore, gN is contemplated for use as a HCMV vaccine. It has been demonstrated that a neutralizing antibody response against HCMV is to a considerable extent strain specific (Klein et al., 1999. J. Virol. 73:878). This previously unrecognized finding suggests that HCMV infection in these cell types is directly involved in the oncogenic process in human cancer, and could lead to new treatment and/or prevention strategies.

The present disclosure includes isolated nucleic acids encoding HCMV polypeptides, such as gN, and the polypeptides encoded by the isolated nucleic acid sequences. Nucleic acids include, but are not limited to, RNA or DNA (either single or double stranded, coding, complementary or antisense), or RNA/DNA hybrid sequences of more than one nucleotide in either single chain or duplex and may include naturally occurring and non-naturally occurring components.

Certain gN sequences are described herein in SEQ ID NOS: 1-10 and elsewhere in the specification. These nucleotides may be expressed and the polypeptides encoded thereby purified in a variety of ways as in well known in the art (for instance, see Sambrook, J., et al., *Molecular Cloning*, Second Edition, 1990, Cold Spring Harbor Press). Expression may be by molecular cloning into an expression vector containing a suitable expression control sequence, such as a promoter and other appropriate transcription regulatory elements and transferring said expression vector into prokaryote or eukaryote host cells, including microbial, yeast, insect and mammalian cells. The expression vectors may be introduced into host cells via any one of a number of techniques including but not limited to transformation, transfection, lipofection, protoplast fusion, and electroporation. Purification methods for isolated expressed protein are well known in the art and within the ordinary skill in the art. Techniques include salt fractionation, ion exchange chromatography, size exclusion chromatography, hydroxylapatite adsorption chromatography, hydrophobic interaction chromatography, immunoaffinity chromatography and affinity chromatography.

Vaccination with inactivated or attenuated organisms, or their products, has been shown to be an effective method for increasing host resistance and ultimately has led to the eradication of certain common and serious infectious diseases. The use of vaccines is based on the stimulation of specific immune responses within a host.

HCMV proteins, especially the membrane bound glycoproteins, are useful in generating an immune response. The gN polypeptide from a given strain of HCMV is contemplated to generate an immune response specific for that strain of HCMV. HCMV polypeptides, such as gN, may be purified from natural sources or produced recombinantly as discussed above. It is contemplated that gN polypeptide from individual strains of HCMV will generate an immune response that is specific for individual strains of gN. The term "immune response" refers to a cytotoxic T cell response or increased serum levels of antibodies specific to an antigen, or to the presence of neutralizing antibodies to an antigen. The immune response is preferably sufficient to make the gN polypeptide useful as a vaccine for protecting human subjects from HCMV infection. Additionally, antibodies generated by the gN polypeptide can be produced and used to detect a HCMV in a body fluid sample. Furthermore, strain specific antibodies generated by the gN polypeptide of specific strains of HCMV can be extracted and used to detect a specific strains of HCMV in a body fluid sample.

The term "protection" or "protective immunity" refers herein to the ability of the serum antibodies and/or cytotoxic T cell responses induced during immunization to protect (partially or totally) against a disease caused by an infectious agent, in this case HCMV. The use of the gN polypeptide as a vaccine is expected to provide protective immunity to humans against HCMV infection by inducing antibodies against HCMV. The use of gN polypeptide from specific strains of HCMV, such as HDu, as a vaccine is expected to provide protective immunity to humans against those strains of HCMV infection by inducing antibodies against those strains of HCMV.

The present disclosure includes a method of generating an immune response and protective immunity to a human against HCMV-mediated diseases. The method includes administering a HCMV polypeptide, such as gN polypeptide, from a specific strain of HCMV, such as HDu, to a human. The gN polypeptide is preferably administered as a formulation comprising a physiologically acceptable carrier and an effective amount of the combined antigen, either with or without an adjuvant. A variety of physiologically acceptable carriers are known in the art, including for example, saline. Routes of administration, amounts, and frequency of administration are known to those skilled in the art for providing protective immunity to a recipient subject. Routes of administration include any method which confers protective immunity to the human recipient, including, but not limited to, inhalation, intravenous, intramuscular, intraperitoneal, intradermal, and subcutaneous. Preferably the gN polypeptide is provided to a human subject by subcutaneous or intramuscular injection. A range of amounts and frequency of administration is acceptable so long as protective immunity of the recipient is achieved. For example, 5 to 20 micrograms can be administered by intramuscular injection between 2 to 4 times over a three month period. Methods and formulations for administering polypeptides can be found in Remmington's Pharmaceutical Sciences. Alternatively, the HCMV nucleic acid may be introduced into a viral vector for expression of the encoded polypeptide in human host cells. The viral vector may then express the polypeptide in an immunogenic form to induce an immune response. Suitable viral vectors include retrovirus (such as lentiviruses), adenovirus, adeno-associated virus, herpes virus, vaccinia virus, polio virus and the like. Alternatively, HCMV nucleic acid can be transferred into cells by non-viral techniques including receptor-mediated targeted nucleic acid transfer using ligand-nucleic acid conjugates or adenovirus-ligand-nucleic acid conjugates, lipofection membrane fusion, electroporation or direct microinjection.

Antibodies to desired HCMV polypeptides, such as but not limited to gN, can be produced by methods known in the art. Such antibodies may include, but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above. Such antibodies may be used, for example, in the detection of HCMV polypeptides or to aid in an immune response.

Methods of detecting HCMV infected cells in a clinical sample are also disclosed. The method may comprise contacting the sample with nucleic acids capable of binding to nucleic acid encoded by HCMV, or with antibodies specific for HCMV. Suitable antibodies and nucleic acid probes are disclosed herein, as well as methods for the detection. The nucleic acid or antibody that has bound to the sample is then detected. In one embodiment, the HCMV polypeptide detected is gN, and the HCMV nucleic acid detected codes for gN. The level of HCMV may be compared to samples confirmed not to contain HCMV.

Diagnostic kits for determining levels of HCMV infection in tissue samples are contemplated. The kits are contemplated to be useful for analysis of HCMV infection for a variety of cell types. These cell types include brain, colon, breast, prostate, ovary and cervix. These kits may rely on the detection of HCMV polypeptides (immunological based kits) or on the detection of HCMV nucleic acid sequences (nucleic acid based methods). Such kits may comprise a HCMV standard, a detecting means for detecting HCMV, an interpreting means to interpret whether the tissue type examined contained HCMV and the accessory components required to perform the assay. The means to interpret may comprise at least one of the following: 1) a negative control; and 2) a positive control.

The HCMV standard may be purified HCMV polypeptide or purified HCMV nucleic acid. In addition, the HCMV standard may be a tissue preparation confirmed to contain a given amount of HCMV. The HCMV polypeptide and HCMV nucleic acid may be selected based on the HCMV polypeptide to be detected in the assay, the HCMV nucleic acid sequence to be detected in the assay, or the HCMV nucleic acid sequence to be amplified in the assay. If more than one HCMV polypeptide or nucleic acid is detected by the assay, then more than one HCMV antigen or nucleic acid standard may be incorporated. The negative control may be a tissue confirmed to lack the presence of HCMV. The positive control may be a tissue sample confirmed to contain HCMV. The positive and/or negative controls may be from the same type of tissue being tested for in the assay or may be from a different tissue. In one embodiment, the positive and negative controls are supplied in lyophilized form. The detecting means may be at least one antibody (preferably monoclonal) or antibody fragments as described above specific to selected HCMV polypeptide (for immunological based kits), or at least one nucleic acid sequence capable of binding to selected HCMV nucleic acid sequences or capable of priming of selected HCMV nucleic acid sequences (for use in assays such as PCR). Accessory components may be compounds, chemicals reagents, labels, buffers, washing reagents, containers and/or equipment.

When antibodies are used as the detecting means, the antibodies employed may be used in several variations. For example, a primary antibody specific for a HCMV polypeptide may be employed. The antibody may be tagged with an appropriate reporter group/labeling reagent for use in a detection system. Alternatively, the primary antibody could be recognized by a secondary antibody tagged with an appropriate reporter group/labeling reagent for use in a detection system. Reporter groups, include, but are not limited to, radioisotopes, fluorescent groups, chemiluminescent groups, luminescent groups, enzymes, and the like. The reporter group may be directly conjugated to the primary or secondary antibody. Alternatively, the primary or secondary antibody may be tagged with a moiety that is capable of specifically binding to the reporter group supplied separately. For example, the secondary antibody may be biotinylated, allowing a binding reaction with a streptavidin/avidin enzyme (such as horse radish peroxidase) reporter group complex. The antibody complex containing the reporter group may be detected by adding the appropriate substrate for detection based on the enzyme used.

When nucleic acids are used as the detecting means, the nucleic acid may comprise at least one nucleic acid probe or primer, as described above, that hybridizes to a selected nucleic acid sequence(s) encoding HCMV. Such a nucleic acid may be used, for example, within a PCR, Northern Blot, Southern blots, slot blots or in-situ hybridization assay, or such similar assays as are known in the art.

Glioma

Malignant gliomas are the most common primary central nervous system (CNS) tumors in humans, have no known etiology, and are generally rapidly fatal despite current therapies. HCMV is known to cause devastating CNS disease in the fetus and immunocompromised adults (Britt et al. 1996 in Fields, B. N., Knipe, D. M., & Howley, P. M., (ed.): Fields Virology $3^{rd}$ Ed., vol 2, Lippincott-Raven, Philadelphia, Pa.: 2493). HCMV gene transcription is activated in inflammatory glial cells (Fritschy et al. 1996 J. Neurosci. 16:2275) and active HCMV infection of glial cells can promote malignant transformation (Doniger et al. 1999). The complex biology of HCMV is suitable for promoting glioma progression. Glioma cells are permissive for productive HCMV infection, and HCMV can acquire mutations leading to persistent infection with minimal cytopathic effect in glioma cells (Poland et al. 1990 J. Infect. Dis.162:1252; Ogura et al. 1986 J. Gen. Virol. 67:2605). In latently infected astrocytes or glioma cells, HCMV expression can be reactivated by inflammatory stimuli (Wolff et al. 1994 Virology 204:101). HCMV is known to dysregulate key tumor related pathways including those affecting cell cycle, DNA stability, apoptosis, angiogenesis, cell migration and invasion, and immune evasion. HCMV can also transactivate other oncogenic viruses in gliomas such as JC virus (Winklhofer et al. 2000 Virology 275: 323; Del Valle et al. 2001 Cancer Res. 61:4287).

The present disclosure shows HCMV proteins and nucleic acids are present in malignant glioma, but not in normal brain or other non-glioma CNS tumors and diseases. HCMV from human gliomas may be transmitted to permissive human fibroblasts in culture. Therefore, there exists a previously unrecognized tight association between HCMV and human malignant glioma, indicating that HCMV may contribute to glioma pathogenesis (Cobb et al. 2002 Cancer Res. 62:3351). The present disclosure indicates HCMV may not conform to conventional paradigms in viral oncogenesis and may involve novel mechanisms that could lead to new treatment or prevention strategies.

Immunohistochemistry (IHC) analysis on paraffin sections from 27 malignant glioma surgical specimens obtained from non-immunocompromised patients using a monoclonal antibody (mAb) specific for HCMV immediately early 1 (IE1-72) protein was used to determine the presence of HCMV in gliomas. IE1-72 immunoreactivity was present in 27/27 malignant glioma biopsy specimens of varying grades (WHO grades II-IV), but not meningioma biopsy specimens or autopsy specimens from patients with Alzheimer's disease, stroke, encephalitis, or no CNS disease (FIG. 1 and Table 1). Malignant glioma cells were heterogeneously immunoreactive for IE1-72, while tumor blood vessels, areas of necrosis, and areas of normal brain without apparent tumor were minimally or not at all immunoreactive. No immunoreactivity of tumor cells was observed in malignant gliomas when primary antibody was excluded, or when an IgG1 isotype identical anti-CD34 mAb antibody specific for blood vessels as used (FIG. 1 and Table 1).

As can be seen in FIG. 1, anti-IE1-72 immunoreactivity is clearly indicated in 4 representative GBMs (A-C & F), a grade II astrocytoma (D) and a grade III oligoastrocytoma (E). Anti-IE1-72 immunoreactivity is absent in normal brain (J). Isotype control anti-CD34 antibody reacts with blood vessels (arrows) in normal (K), but not tumor cells (L).

To further assess the extent of HCMV protein expression, IHC analysis was performed on a subset of these glioma specimens using mAbs specific for: 1) HCMV pp65 tegument protein and 2) HCMV 76 kD early protein and 52 kD delayed-early DNA binding protein, as well as IE1-72. Anti-IE1-72 (G), anti-p52/anti-76kD (H), and anti-pp65 (I) immunoreactivity is seen in different sections from the same GBM. A giant tumor cell shows nuclear and cytoplasmic pp65 immunoreactivity (arrow in I).

Immunoblots were performed on protein lysates from frozen tissues of 7 GBMs and 1 control brain specimen with a MAb specific for pp65 to confirm the presence of HCMV proteins. pp65 protein was detected in 6/7 GBM lysates but not in normal brain tissue. Specificity of the anti-pp65 antibody was confirmed by repeating the experiment after pre-absorbing the antibody with baculovirus-expressed pp65 recombinant protein, which eliminated reactivity for the pp65 protein.

Figure 2:
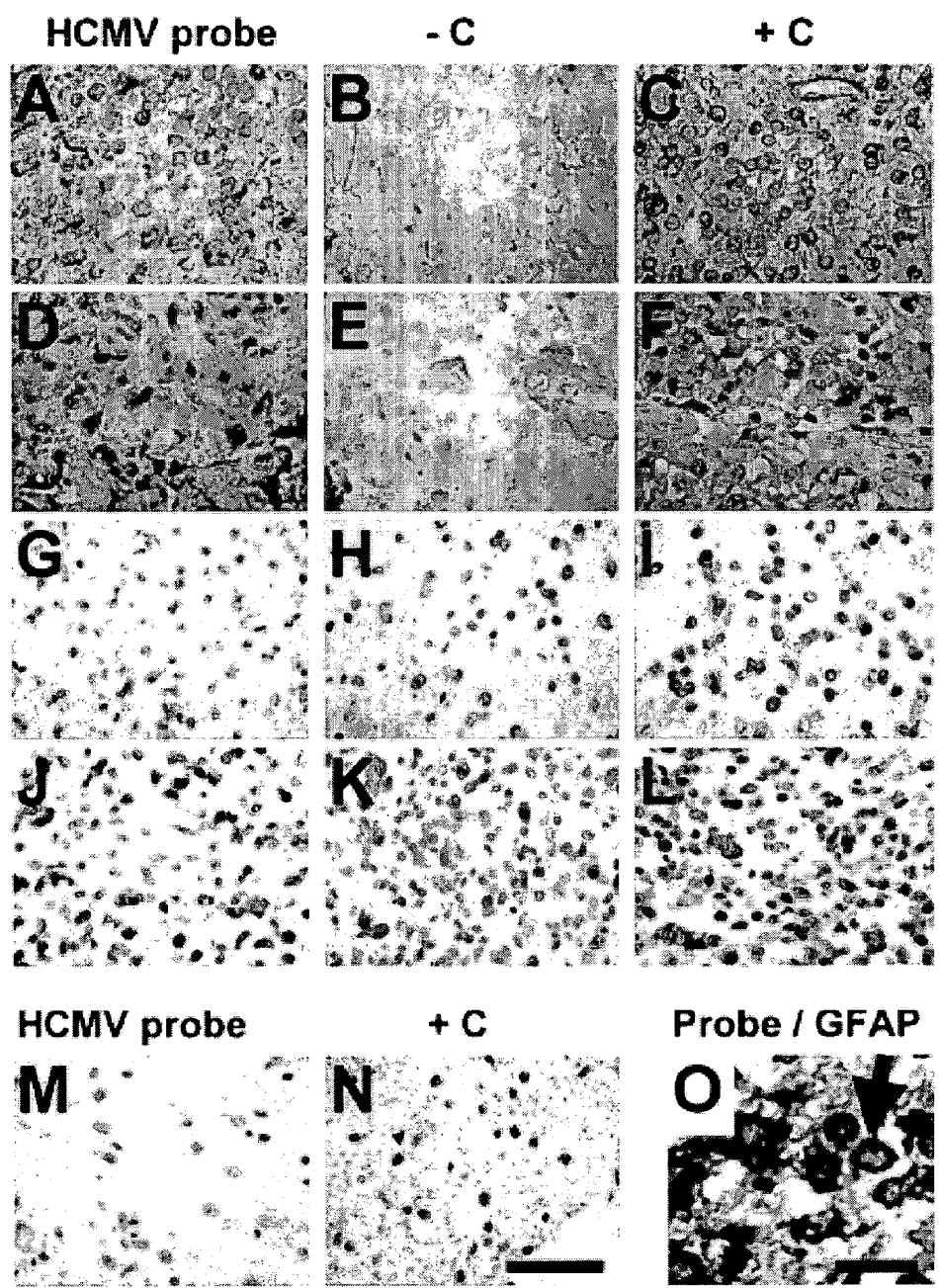
FIG. 2 shows in situ hybridization for HCMV nucleic acids using two different probes in a grade II astrocytoma (A-C, G-I) and a GBM (D-F, J-L). HCMV nucleic acids are detected with a biotinylated 21-base oligonucleotide probe specific for HCMV IE1-72 mRNA in a grade II astrocytoma (A) and GBM (D) (purple, chromogen NBT). B and E, negative controls where no probe was added (identical result was obtained when a biotinylated probe specific for HSV-1/2 was used). C and F, poly(thymidylic acid)-positive control probe hybridizes with RNA in both tumors. Hybridization with HCMV nucleic acids is observed in the same grade II astrocytoma (G) and GBM (J) with a digoxigenin-labeled DNA probe specific for the entire HCMV genome (brown, chromogen, DAB). A digoxigenin-labeled negative control probe does not hybridize with nucleic acids in these tumors (H and K). A positive control digoxigenin-labeled probe specific for alu-DNA repeats hybridizes with nucleic acids in tumors (I, L) and normal brain control (N). No hybridization is detected in normal brain with the digoxigenin-labeled probe specific for HCMV DNA (M). O, Double-labeled cells: ISH with HCMV genomic DNA probe (chromogen DAB), and IHC with anti-GFAP antibody (chromogen NBT) illustrates positive brown nuclei surrounded by dark blue GFAP-positive cytoplasm in a GBM. Sections G-N are counterstained with hematoxylin (blue). Bars: A-N, 100 μm; O, 40 μm.

HCMV nucleic acids are present in the same cellular distribution as HCMV proteins in these tumors as demonstrated by in situ hybridization (ISH) (see FIG. 2 and Table 2). To detect IE1-72 nucleic acids, ISH was performed in gliomas (a grade II astrocytoma and a GBM) and control tissues with a 21-base oligonucleotide probe specific to IE1-72 mRNA (ResGen/Invitrogen). As controls, a 21-base biotinylated probe specific for HSV 1/2 DNA was used (ResGen/Invitrogen), a combination probe specific for HPV types 6/11/16/18/31/33 consisting of 6 biotinylated oligonuclotides (InoGenex), or no probe (diluent only). A biotinylated probe specific for poly-A RNA was used as a positive control (ResGen/Invitrogen). HCMV nucleic acids were detected in a grade II astrocytoma (A) and a GMB (D), but not in controls (B and E). No signal was detected when this HCMV probe was substituted with a similar probe specific for HSV-1/2, or when probe was eliminated from the hybridization reaction. A positive control probe (specific for poly-A mRNA) hybridized with all specimens analyzed (C and F).

Hybridization with HCMV nucleic acids is observed in the same grade II astrocytoma (G) and GBM (J) is probed with a digoxigenin-labeled DNA probe specific for the entire HCMV genome. A digoxigenin-labeled negative control probe does not hybridize with nucleic acids in these tumors (H and K). A positive control digoxigenin-labeled probe specific for alu-DNA repeats hybridizes with nucleic acids in tumors (I and L) and normal brain control (N). No hybridization is detected in normal brain with the digoxigenin-labeled probe specific for HCMV DNA (M). Double labeling experiments confirmed that HCMV DNA was present in cells of glial origin. Cells were double-labeled cells by ISH with HCMV genomic DNA probe, and IHC with anti-GFAP antibody. Panel 0 illustrates positive brown nuclei surrounded by dark blue GFAP-positive cytoplasm in a GBM.

In glioma specimens that invaded normal brain, HCMV nucleic acids and IE1-72 protein expression are easily detected in areas of tumor but are minimally or not detected in areas of normal appearing brain within the same section (FIG. 1, panels C and D). The specificity of the HCMV oligonucleotide ISH probe and anti-IE 1-72 mAb in gliomas was confirmed using HCMV (AD169, moi 5-10) infected human U251 glioblastoma multiforme (grade IV astrocytoma/GBM) cells in culture. Signal for HCMV nucleic acids and IE1-72 protein was strong after 24 hours in AD169-infected U251 cells, but was not detected in uninfected U251 cells.

For PCR, samples were obtained from frozen specimens, or from paraffin sections of glioma specimens that were positive for HCMV nucleic acids by ISH. DNA was extracted from the frozen tissues or paraffin samples and used to supply DNA for the PCR reactions. HCMV nucleic acid expression in gliomas was characterized using RT-PCR in a blinded fashion on RNA extracted from frozen surgical specimens of 1 grade II astrocytoma, 8 GBMs and 4 control brains. PCR primers specific for the UL55 (glycoprotein B, gB) gene of HCMV were used. UL55 mRNA was detected in the astrocytoma and 8/8 GBMs (T1-T9), while none was detected in the control brains (nb1-nb4) (FIG. 3A). No bands were observed when the PCR reaction was repeated in the absence of reverse transcriptase. The PCR products were cloned and sequenced from 9 of these GBMs. 3/9 samples showed a gB-1 (Towne prototype) genotype. 4/9 had a gB-2 (AD 169 phenotype) genotype, while 2/9 showed a variation of either phenotype.

Figures 3, 3B:
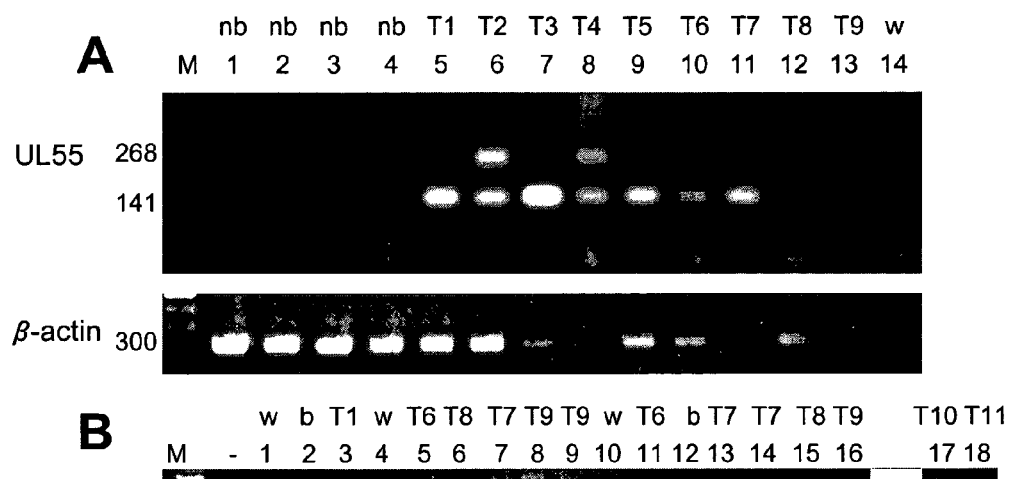
FIGS. 3A and B show agarose gels illustrating PCR amplification (2×30 cycles) of UL55 (FIG. 3A) and UL73 (FIG. 3B). In A, DNA was obtained from normal brain (lanes 1-4), a grade II astrocytoma (T1, lane 5) and 8 GBMs (T2-9, lanes 6-13). Lane 14 is a control lane containing water only. DNA from the tumors was extracted from paraffin embedded samples, while DNA from normal brain was extracted from frozen specimens. External primer amplifiers are identified in some samples at 268 bp. PCR of B-actin confirms that all specimens contained DNA, although the DNA extracted from the paraffin specimens is more degraded. As can be seen UL55 DNA was amplified from the astrocytoma and 8 GBM specimens, but not from the normal brain specimens. In B, DNA from several of the same paraffin embedded specimens in A was amplified for UL73. Samples T1 (lane 3), T6 (lanes 5 and 11), T7 (lanes 7, 13 and 14), T10 (lane 17) and T11 (lane 18) show amplified UL73 product at 355 bp. The bands from samples T1, T6 and T10 were excised and DNAs extracted for reamplification with 30 cycles of PCR using the same primers. The PCR products were then submitted for direct DNA sequencing. The amplified DNA in TII was sent directly for direct DNA sequencing without reamplification. Water (w) and blank paraffin specimens (b) were used as negative controls.

In addition, nested PCR was performed on glioma specimens to detect the presence of UL73 (glycoprotein N, gN) (FIG. 3B). Several of the samples that were analyzed for UL55 (T1, T6, T7, T8, and T9), and two GBMs (T11 and T12) that were not previously analyzed, were analyzed for UL73 nucleic acid expression. For UL73, PCR primers were directed to a hypervariable region of gN. UL73 products were detected in 3/5 GBM (T1, T6 and T7) samples which had previously tested positive for UL55. In addition, UL73 was detected in 2/2 GBM frozen samples not tested for UL55. The DNA sequence of the PCR products from 4 of these PCR reactions was extracted and subject to direct DNA sequencing. The DNA sequence of 4/4 of the samples were closely homologous to a clinical strain of HCMV, HDu. HCMV strain HDu is distinct from known laboratory strains. This finding suggests that a glioma specific, and perhaps tumor specific, strain of HCMV exists and that HDu is this strain. The HDu strain has significant genomic variability when compared to laboratory HCMV strains. These findings are consistent with previous findings indicating no correlation between UL55 and UL73 genotypes among different HCMV strains (Pignatelli et al. 2001. J. Virol. 82:2777).

Figure 4A:
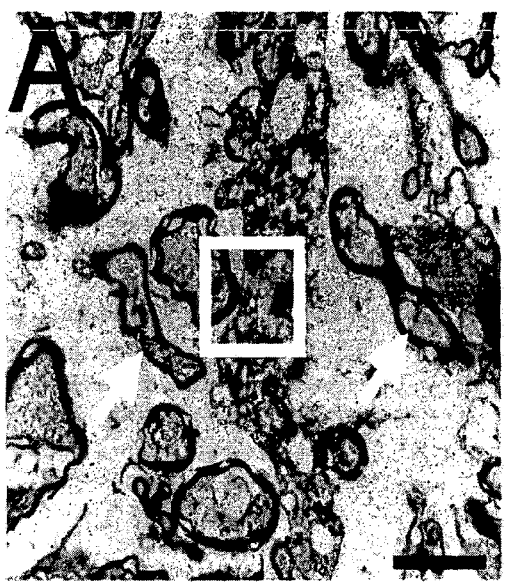
FIGS. 4A and B show immunogold electron micrograph of anti-pp65 monoclonal antibody reactivity in an invasive human GBM tumor specimen.
Figure 4B:
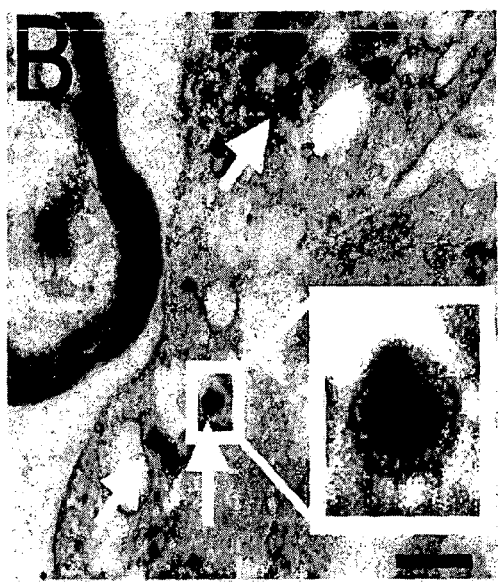
In FIG. 4B, a 70,000× view of boxed area from (a) shows a round electron-dense particle morphologically consistent with HCMV labeled with a 35 nm gold particle in the cytoplasm of the cell. Bar, 200 nm.

HCMV viral particles were identified in human gliomas. Two GBMs obtained at the time of surgery were analyzed by immunogold electron microscopy (EM-111C) using an anti-pp65 mAb labeled with a secondary mAb bound to gold particles. In both tumors, electron-dense particles consistent with the morphology of HCMV virions and dense bodies were labeled with gold. Electron microscopy from 1 sample is shown in FIGS. 4A and B. In FIG. 4A, multiple electron dense particles ranging from 150-250 nm are observed (arrows) in a cell surrounded by myelinated axons (open arrows)

at 8,000× (bar, 1 μm). In FIG. 4B, a 70,000× view of boxed area from FIG. 4A shows a round electron-dense particle morphologically consistent with HCMV labeled with a 35 nm gold particle in the cytoplasm of the cell (bar, 200 nm).

Figure 5:
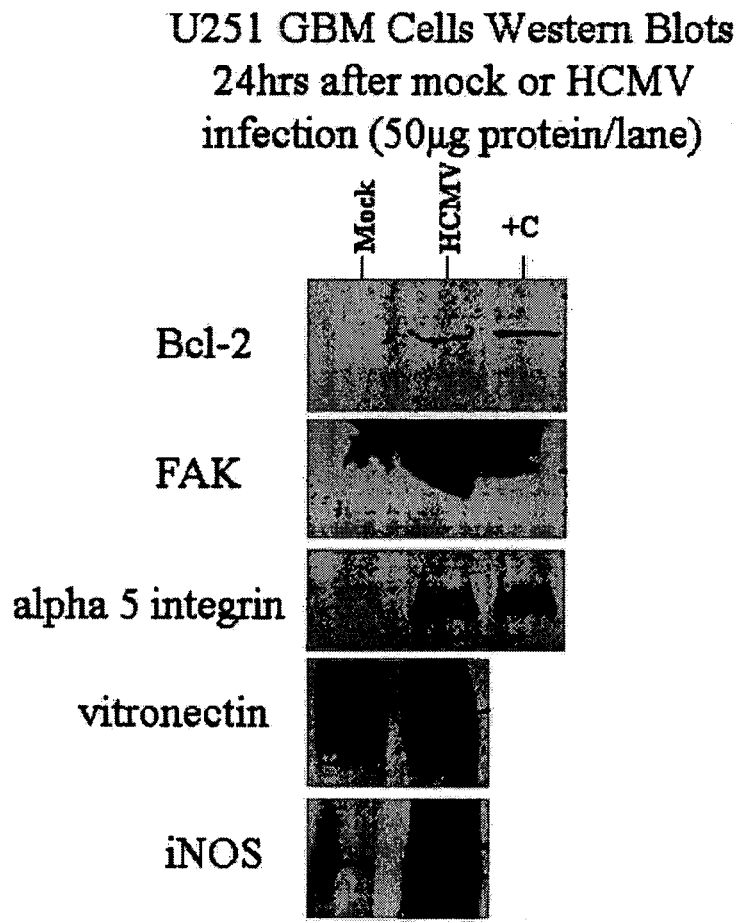
FIG. 5 shows alterations of protein expression in U251 cells infected with HCMV Towne. 24 hours after infection with HCMV Towne, or mock infection, U251 cell protein was harvested according to standard laboratory procedures. 50 ug of protein was loaded per lane on polyacrylamide gels. Several proteins important in malignant glioma angiogenesis (iNOS), apoptosis (Bcl-2), mitogenesis (focal adhesion kinase, FAK), and invasion (α5 integrin, vitronectin, Bcl-2 and FAK) are induced in infected U251 cells compared to mock infected cells after 24 hrs. Proteins were visualized with appropriate antibodies according to established laboratory procedures.

To determine the influence of HCMV infection on tumor pathways relevant to oncogenesis, in vitro experiments with HCMV infection of tumor cells were conducted. For these studies the human malignant glioma cell line (U251) was used since human glioma cells can sustain a widespread productive HCVM infection, and the biological properties of these cells are well documented. In order to determine if HCMV infection of U251 cells induced expression of tumor promoting proteins, U251 cells were infected with HCMV Towne strain. FIG. 5 shows that several proteins important in malignant glioma angiogenesis (iNOS), apoptosis (Bc1-2), mitogenesis [focal adhesion kinase (FAK)], and invasion (α5 integrin, vitronectin, Bc1-2 and FAK) are induced in infected U251 cells compared to mock infected cells after 48 hrs.

Figures 6A, 6B, 6C:
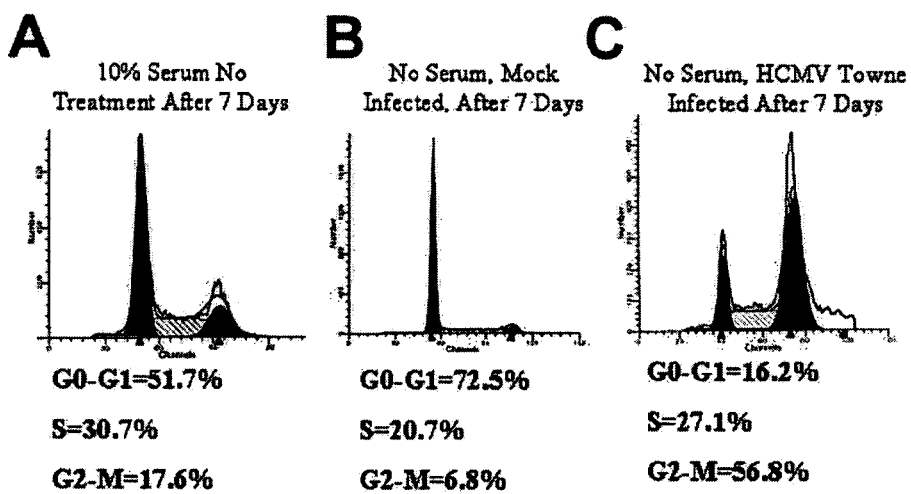
FIGS. 6A-C show alteration of cell cycle progression in HCMV infected U251 cells. Randomly cycling U251 cells were either maintained in DMEM+10% FBS for 7 days (FIG. 6A), or were serum-starved (0%) for 7 days after mock infection (FIG. 6B), or were serum-starved (0% FBS) for 7 days after infection with HCMV Towne at an moi 5-10 pfu (FIG. 6C). Cell cycle progression was assessed by propiduim iodide staining followed by flow cytometry. Mock infected serum-starved cells are arrested in G0/G1 (72%)

To determine if HCMV can dysregulate cell cycle checkpoint controls, experiments using flow cytometry of propidium iodide-stained U251 cells were performed. HCMV infection deregulates the G1/S transition checkpoint in U251 cells. Previous investigators have shown the HCMV IE1 and IE2 gene products can promote cell entry into the cell cycle with a resulting arrest in G1 or G2/M, based on the phase of the cell cycle the cells are in when transfected (Castillo et al. 2000 J Virol 74: 8028; Murphy et al. 2000 J Virol 74: 7108). Mock infections and HCMV Towne infections were performed on randomly cycling U251 cells in 10% serum and then transferred the cells to 0% serum for 7 days (FIG. 6A). We found that, as opposed to the mock-infected cells that arrested in G1/G0 (FIG. 6B), HCMV infected cells were shifted from G0/G1 to G1/S and G2/M phase (FIG. 6C). These results indicate a profound effect of HCMV on tumor cells with respect to disinhibition of cell cycle regulatory pathways.

Figure 7A:
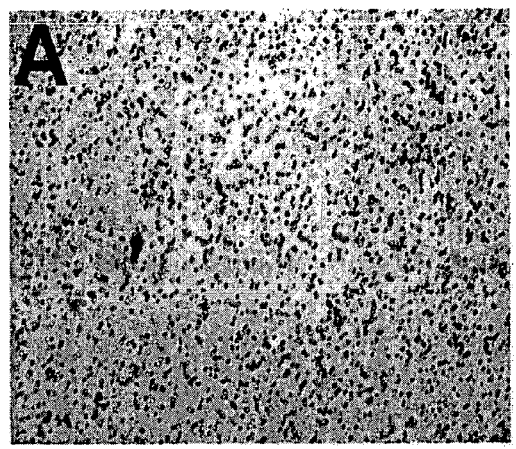
FIG. 7 shows alterations in invasive potential of U251 cells after transfection with HCMV Towne. Panel A illustrates control (mock infected) U251 cells, with only rare cells (stained purple) able to invade through the extracellular matrix (ECM) and the 8 um pores (dark holes). In panel B, after HCMV infection, a high percentage of U251 cells have invaded the ECM and migrated through the pores as indicated by the increased number of cells staining purple. The cell invasion assay was purchased from Chemicon (Catologue no. ECM550) and performed as per the manufacturer's instruction.
Figure 7B:
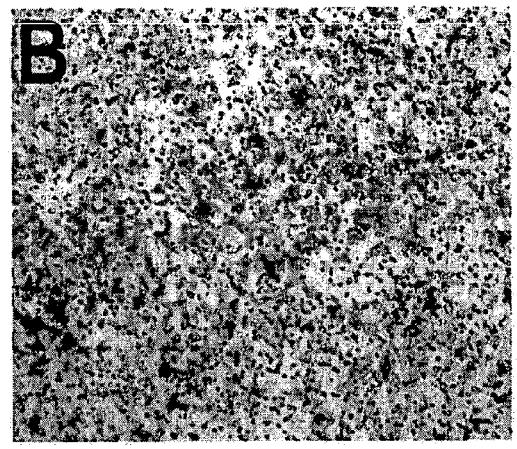

HCMV-infected U251 cells also display dramatically increased invasive properties when compared to non-HCMV infected cells. FIG. 7 illustrates the results of HCMV infected cells using a commercial Boyden chamber-like in vitro invasion assay (Chemicon Cell Invasion Assay™, cat. # ECM550). With control (mock infected) U251 cells (FIG. 7A), only rare purple-stained cells are able to invade through the ECM and 8 μm pores (dark holes). After HCMV infection, a large percentage of U251 cells have invaded the ECM and migrated through pores (multiple purple cells are seen; FIG. 7B). These data indicate that HCMV induces alteration in extracellular matrix proteins and proteases that enhance tumor cell invasion through a complex basement membrane matrix (Matrigel®).

Prostate Cancer

Prostate cancer is the most common male cancer in the US and the Western world, and the second leading cause of male cancer death in the US. Recent epidemiological studies indicate a significant association between prostate cancer incidence and multiple sexually transmitted diseases (STDs), suggesting that a sexually transmissible agent or agents increase the risk of prostate cancer (Dennis et al 2002 Epidemiology 13:72; Hayes et al. 2000 Br J Cancer 82:718). To date, no specific infectious agents have been causally linked to prostate cancer, although detection of specific human papilloma virus (HPV) DNA sequences in human PC specimens has indicated a possible role for this viral factor (Dodd et al. 1993 J Urol 149:400; McNicol et al. 1991 J Urol 145:850) Other viral factors are also associated with STDs and sexual contact. In adults, sexual contact is the major route of HCMV transmission, and increased HCMV seropositivity rates in adults are associated with an increased history of STDs (Britt et al. 1996 in Fields, B. N., Knipe, D. M., & Howley, P. M., (ed.): Fields Virology 3$^{rd}$ Ed., vol 2, Lippincott-Raven, Philadelphia, Pa.: 2493). During active infection in non-immunocompromised hosts, HCMV is shed from the genital tract of both males and females, and in males attending STD clinics, multiple HCMV strains can be cultured from semen (Drew et al. 1984 Ann N.Y. Acad Sci 437:320).

Early studies indicated that HCMV had direct transforming properties with respect to prostatic epithelial cells and suggested that particular strains of HCMV, possibly mutant strains, at low levels of infection could be found in prostate cancer specimens from patients (Geder et al. 1977 Cancer Treat Rep 61:139; Sanford et al. 1977 J Urol 118:789; Rapp et al. 1975 J Virol 16:982) The present disclosure shows a >90% prevalence of HCMV infection and expression in prostate cancer biopsy specimens from non-immunocompromised individuals.

IHC, ISH, and PCR was performed on paraffin-derived biopsy specimens of human prostate adenocarcinomas and prostatic intraepithelial neoplasia (PIN) lesions to determine whether HCMV is present in these specimens. Using IHC with a mAb specific to HCMV IE1-72 (BioGenex®), HCMV was detected in 18/19 PIN and adenocarcinoma lesions (Table 3). In these tumors IE1-72 protein is specifically highly expressed in cell nuclei in areas of basal cell hyperplasia and in nuclei cytoplasm in prostatic intraepithelial neoplasia (PIN) lesions, but not expressed or only minimally expressed in normal or invasive adenocarcinoma epithelial cells. IHC with a mAb specific to the HCMV delayed tegument protein pp65 (Novacastra™) showed results consistent with the pattern of IE1-72 protein expression, except that pp65 was expressed more often in the invasive tumor than the PIN lesions (Table 3). Taken together the patterns of IE1-72 and pp65 expression indicate that HCMV is strongly associated with PIN and prostate carcinoma lesions, and that tumor cell differentiation state may influence HCVM gene expression or that HCVM influences tumor differentiation state. These findings also suggest that nuclear and cytoplasmic protein trafficking of IE1-72, an oncogenic protein, may be regulated differently based on cell differentiation state.

Figure 8:
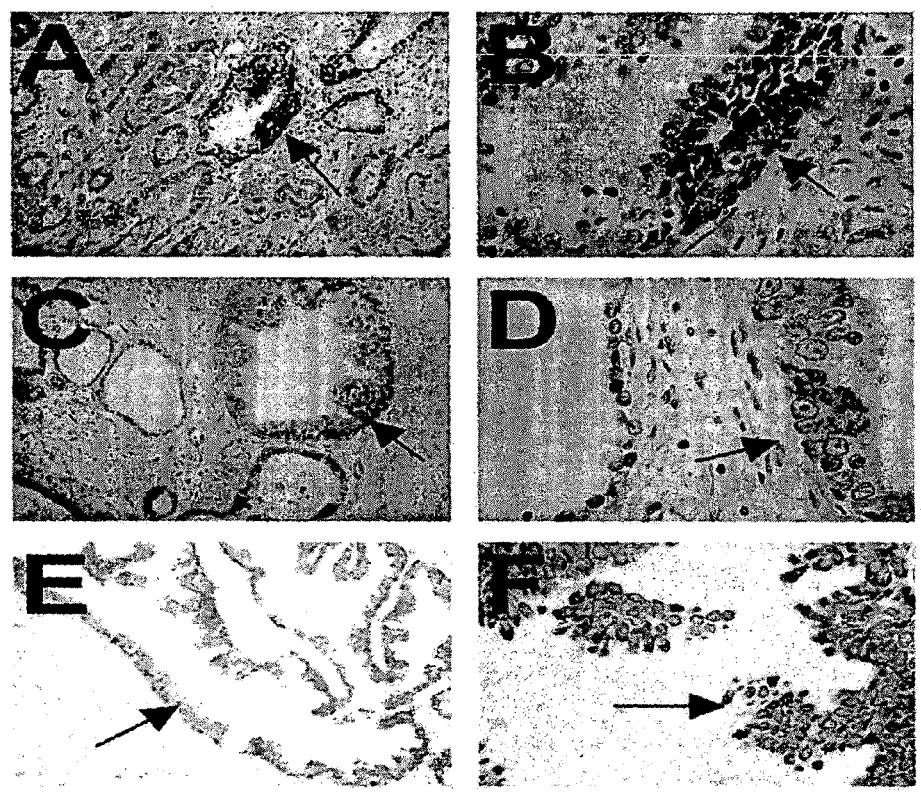
FIG. 8 shows immunohistochemical localization of HCMV proteins in human PIN/prostate cancer (A-D) and PIN (E and F). IHC negative controls were performed with an $IgG_1$ isotype-identical mAb to CD34 (BioGenex®). CD34 immunoreactive blood vessels were observed in all tumors, but no tumor cell immunoreactivity was observed (Table 3).

FIG. 8 illustrates IE1-72 mAb IHC in two representative biopsy specimens from patients with PIN/prostate cancer (FIG. 8, A-D) and PIN (FIG. 8, E, F). Small arrows in A and B indicate intense nuclear IE1-72 immunoreactivity in an area of basal cell hyerplasia surrounded by minimally to non-immunoreactive areas of invasive carcinoma. Another area of tumor from the same patient illustrates intense IE1-72 immunoreactivity in a high-grade PIN lesion (arrows) while minimal to no immunoreactivity is noted in adjacent normal epithelium (FIG. 8, C and D). IE1-72 IHC from a needle biopsy of another patient shows intense PIN immunostaining with low and high power views (FIG. 8, E and F). As a negative control, IHC was performed with an IgG$_1$ isotype-identical mAb to CD34 (BioGenex®), which is specific for blood vessels, on most of these specimens. CD34 immunoreactive blood vessels were observed in all tumors, but no tumor cell immunoreactivity was observed (Table 3). The data in FIG. 8 and Table 3 clearly indicates that HCVM proteins are detected in a very high percentage of prostatic pre-malignant and malignant lesions.

To detect IE1-72 nucleic acids in these tumors, ISH was performed with a 21-base oligonucleotide probe specific to IE1-72 mRNA (ResGen/Invitrogen). As controls, a 21-base biotinylated probe specific for HSV 1/2 DNA was used (ResGen/Invitrogen), a combination probe specific for HPV types 6/11/16/18/31/33 consisting of 6 biotinylated oligonuclotides (InnoGenex), or no probe (diluent only). A biotinylated probe specific for poly-A RNA was used as a positive control (ResGen/Invitrogen). IE1-72 nucleic acid was detected in neoplastic epithelium in areas of PIN and invasive prostate cancer in 4/4 of tumors tested which were known to be immunoreactive for IE1-72 protein (Table 3).

Figure 9:
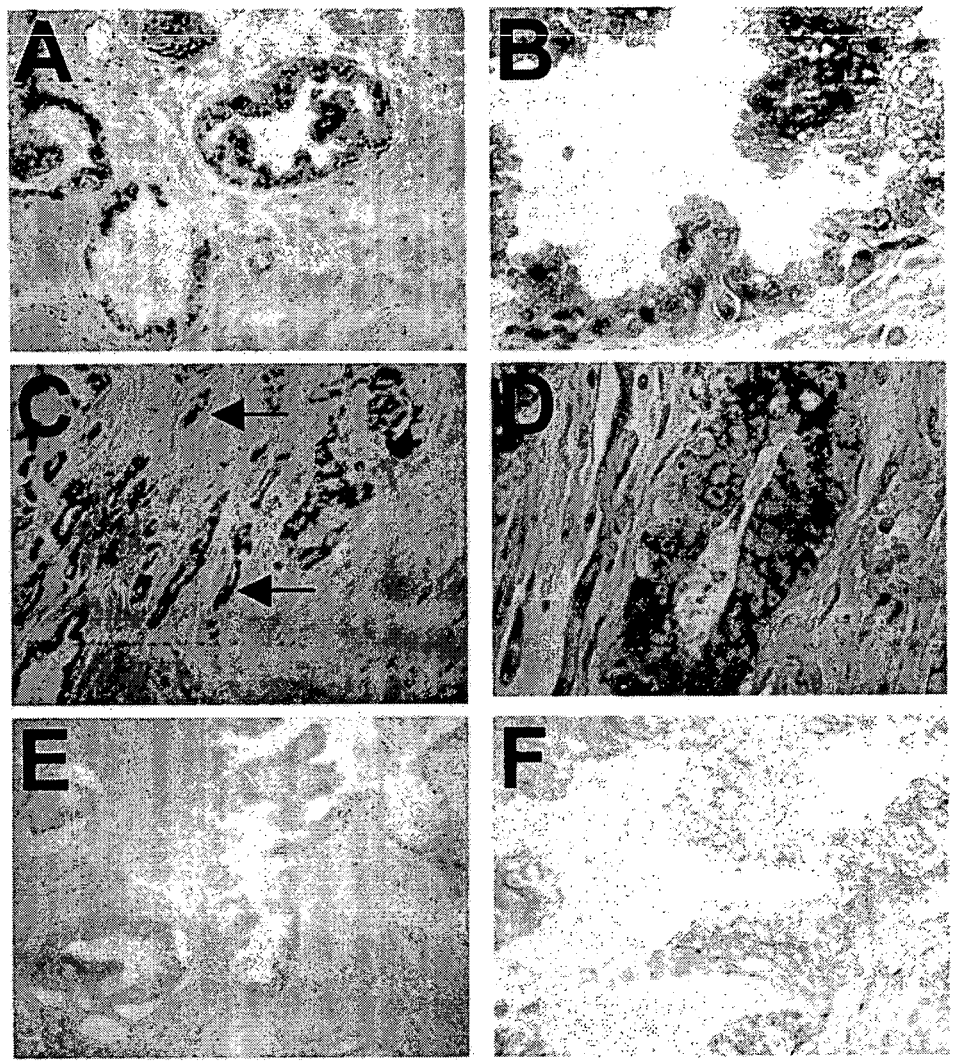
FIG. 9 shows in situ hybridization for HCMV nucleic acids using a biotinylated 21-base oligonucleotide probe specific for HCMV IE1-72 mRNA. Two different paraffin-embedded biopsy specimens (from the same patient shown in FIG. 8, A-D) that illustrate evidence of HCVM IE1-72 nucleic acid hybridization at low and high power in areas of PIN (A and B) and in invasive tumor areas (arrows in C and D). The HSV 1/2 and HPV probes were negative in this tumor (HPV probe shown in E and F).

Interestingly, IE1-72 nucleic acids were detected in both areas of PIN and invasive carcinoma, whereas IE1-72 protein expression was only detected in areas of PIN. These data indicate that transcriptional or translational regulation of HCMV gene products might be regulated differently in PIN lesions compared to higher-grade infiltrative lesions. FIG. 9 shows two different paraffin biopsy specimens (from the same patient shown in FIG. 8, A-D) that show IE1-72 nucleic acid hybridization at low and high power in areas of PIN (FIG. 9, A and B) and in invasive tumor areas (FIG. 9, C and D). The HSV 1/2 and HPV probes were negative (HPV probe shown in FIG. 9, E and F).

DNA was extracted from paraffin sections several of the same specimens in which HCMV nucleic acids and IE1-72 expression were demonstrated. From 10 of these specimens, the hypervariable region of the HCMV genome corresponding to ORF UL73 (gN) was amplified with UL73 specific primers. No DNA was amplified from water or blank paraffin block controls (n=8). The extracted DNA from the 10 specimens was sequenced. The sequence of the UL73 regions is given in SEQ ID NOS. 1-10. The UL73 sequences of all 10 were closely homologous to a clinical strain of HCMV, HDu. HCMV strain HDu is completely distinct from any known laboratory strains. These findings suggest that a prostate specific, and perhaps tumor specific, strain of HCMV may exist and that HDu may be this strain.

Colorectal Cancer

Colorectal cancer is the second leading cause of cancer death in the industrialized nations and most cases occur sporadically without a clear etiology or genetic predisposition (Fearon et al. 2001. Cancer: Principles and practice of oncology. 6th Ed. Lippincott Williams and Wilkins, Philadelphia, Pa. 1037-1049). Epidemiological studies suggest that environmental factors and host immunological characteristics are likely to contribute to the initiations and progression of colon cancer. The present disclosure shows HCMV early and late proteins and nucleic acids are detected in a high percentage of colorectal adenocarcinoma specimens, and are not detected in adjacent non-neoplastic colon. Furthermore, HCMV gene products are strongly associated with early and intermediate stages of colon adenocarcinoma and less with poorly differentiated adenocarcinomas. These findings are the first to demonstrate that HCMV proteins and nucleic acids are associated with a high percentage of human colorectal polyps and adenocarcinoma (Harkins et al. 2002, Specific Localization of human cytomegalovirus nucleic acids and proteins in human colorectal cancer, Lancet 2002 Nov. 16;360(9345): 1557-63) This suggests that HCMV contributes to mutagenesis and cellular dysregulation and contributes to the early multistep processes leading to frank malignancy in human colorectal cancer.

Figure 10:
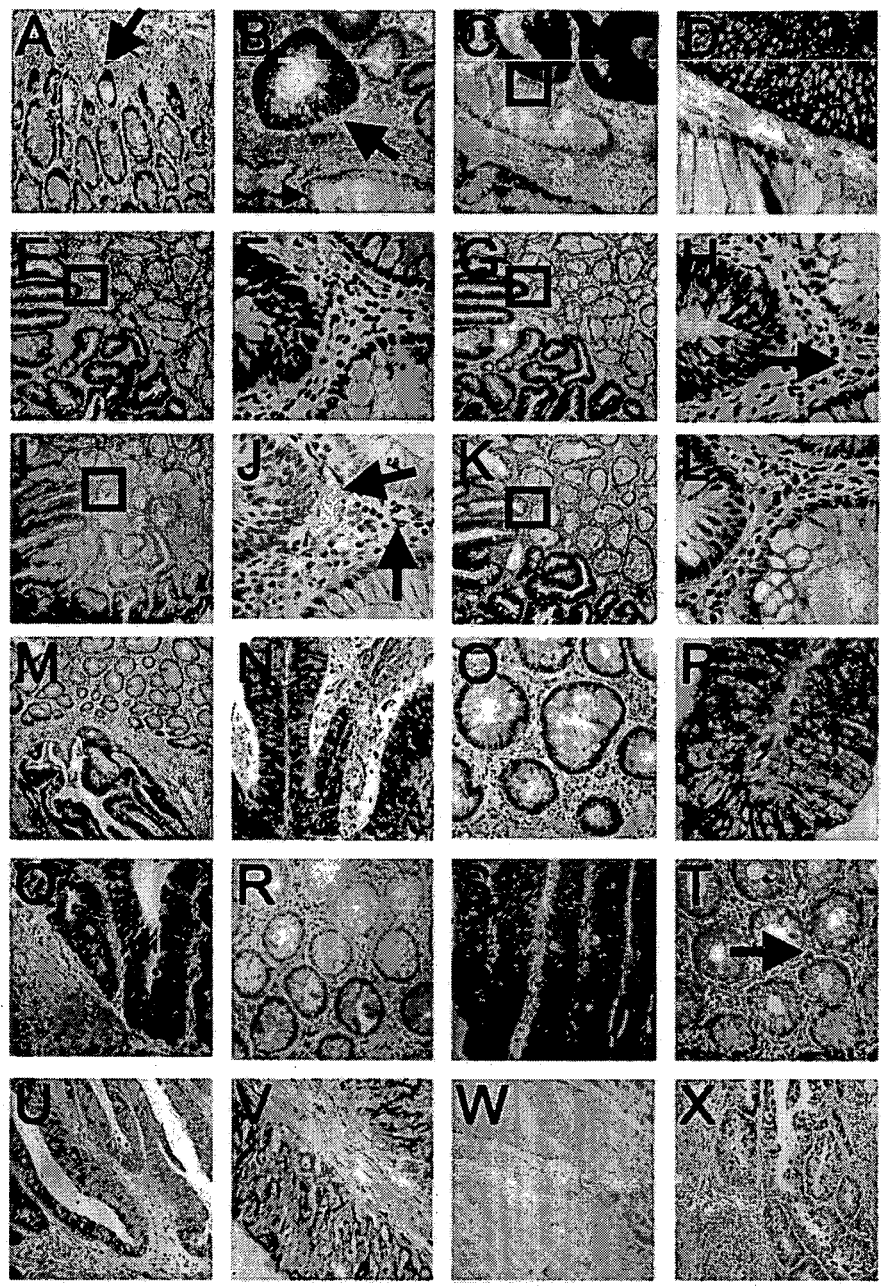
FIG. 10 shows immunohistochemistry and in situ hybridizaton for HCMV proteins and nucleic acids in human colonic polyps and adenocarcinomas. IE1-72 immunoreactivity (brown staining) is identified at the basal crypts in a hyperplastic polyp (arrow in panel A) and in dysplastic crypts in a tubular adenoma (large arrow in panel B) but not in adjacent normal appearing colon epithelium (small arrow in panel B). IE1-72 immunoreactivity is identified in malignant appearing cells but not adjacent normal-appearing epithelium in a colon adenocarcinoma at low (panel C) and high power (panel D, boxed area in C). Sequential sections a colon adenocarcinoma at low and high power (boxed areas) illustrate similar pattern of immunoreactivity for IE1-72 (panels E and F) and pp65 (panels G and H), except that inflammatory cells are also immunoreactive for pp65 in areas adjacent to tumor (arrow in panel H). Only blood vessel immunoreactivity is noted after CD-34 immunostaining (negative control) of same area (panels I and J; arrows in J show endothelial cell staining). Diffuse COX-2 immunoreactivity is noted in this adenocarcinoma as well (panels K and L). Low (panel M) and high power (panels N-P) images of a different colon adenocarcinoma reveal IE1-72 immunoreactivity in an area of tumor (panels N and P) but not adjacent normal crypts (panel O). pp65 immunoreactivity was also present in this same tumor (panel Q) but not in adjacent normal epithelium (panel R). COX-2 immunoreactivity correlated well with IE1-72 and pp65 immunoreactivity in this tumor with COX-2 immunoreactivity present diffusely in tumor areas, but only in inflammatory cells in adjacent normal appearing epithelium (arrow in panel T). Low and high power images of in situ hybridization studies using a probe specific for HCMV RNA illustrate hybridization with colon adenocarcinoma epithelium (panels U and V). No hybridization was observed when probe was omitted (panel W). Positive control probe hybridization (specific for poly-A mRNA) is shown in panel X. Original magnification×40 (E, G, I, K, M, U, W, X),×100 (A, B, C, N, O, Q, R, S, T),×400 (D, F, H, J, L, P, V).

To determine if HCMV was present in human colorectal cancers, IHC analysis was performed on paraffin sections of neoplastic and non-neoplastic colon surgical specimens with a monoclonal antibody specific for the HCMV IE1-72 (Goldstein et al. 1982 Infection and Immunity 38:273-281). As shown in Table 4, IE1-72 was detected in 14/17 polyps and 12/15 adenocarcinomas. IE1-72 protein was not detected in normal appearing colonic mucosa adjacent to areas or tumor within the same pathological sections, and no IE1-72 immunoreactivity was detected in 7/7 non-neoplastic colon tumorfree margin biopsy specimens from 7 of these same patients. Thus, 82% of polyps and 80% of adenocarcinomas were immunoreactive for IE1-72 while IE1-72 immunoreactivity was detected in 0% of adjacent non-neoplastic colon sections FIG. 10 shows the results of the IHC studies. In hyperplastic polyps, IE1-72 was minimally detectable, and was found mostly in cells at the base of colonic crypts (A) In tubular adenomas, IE1-72 immunoreactivity was detected in areas of dysplastic epithelium and generally not detected in areas of normal appearing colonic crypts (B). Colonic crypts immunoreactive for IE1-72 typically displayed morphological characteristics of dysplastic aberrant crypt foci (ACF), with increased nuclear/cytoplasmic ratios, lack of uniform architecture, and nuclear migration away from the basement membrane (B-D). In moderately and well-differentiated colon adenocarcinomas, IE1-72 immunoreactivity was found throughout the neoplastic epithelium and was notably absent in adjacent areas of normal appearing colonic crypts (C, D, M-P). Little if any IE1-72 immunoreactivity was detected in areas of poorly differentiated adenocarcinoma, even when well-differentiated areas of tumor within the same specimen showed strong IE1-72 immunoreactivity. Negative controls for IE1-72 immunohistochemistry (elimination of IE1-72 antibody from the reaction and/or substituting IE1-72 antibody with an equivalent concentration of anti-CD34 IgG1 isotype-identical monoclonal antibody, specific for endothelial cells) were performed and did not result in tumor cell immunoreactivity (Table 4 and I and J).

A subset of these specimens was evaluated for expression of delayed HCMV protein expression by performing IHC with a monoclonal antibody specific for the HCMV pp65 tegument protein. pp65 immunoreactivity was detected in neoplastic epithelium and inflammatory cells in neoplastic tumors (Table 4, G, H, Q and R), thus corroborating the IE1-72 immunoreactivity. pp65 immunoreactivity was not detected in non-neoplastic colon specimens (G, H, Q and R). In adjacent sections of the same tumor specimen, the pattern of pp65 immunoreactivity closely correlated with the pattern of IE1-72 immunoreactivity (E-H). Negative controls for pp65 antibody were performed as for IE1-72 with similar results (Table 4). Similar to what was seen for EE1-72, pp65 protein was detected in 8/10 polyps and 10/10 adenocarcinmoas while non-neoplastic colon from 2 of the same patients who donated polyp or adenocarcinoma specimens as negative for pp65 expression.

To confirm that the IE1-72 and pp65 mAbs were specific for HCMV and to demonstrate the presence of HCMV nucleic acids in these sample, in situ hybridization (ISH) was performed on paraffin sections of several of the tumor specimens that were immunoreactive for IE1-72. To detect HCMV nucleic acids, a biotinylated 21-base oligonucleotide probe specific for HCMV immediate early gene mRNA was used. As with the IE1-72 and pp65 IHC staining, the biotinylated oligonucleotide probe demonstrated hybridizaton with HCMV nucleic acids in neoplastic colon epithelium in multiple specimens (Table 4, FIG. 10, panels U-X). As negative controls for the biotinylated probe, either probe was eliminated from the reaction or a biotinylated 21-base oligonucleotide probe with a similar GC content specific for HSV-1/2 mRNA was used. As a positive control, a biotinylated probe specific for poly-A RNA sequences was used.

Figure 11:
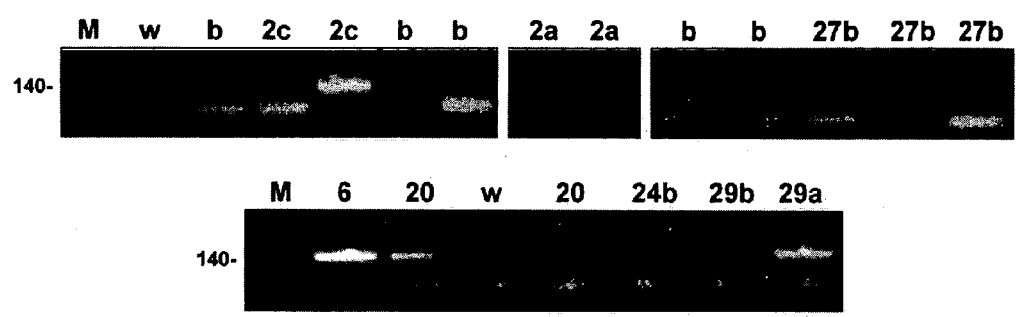
FIG. 11 shows nested PCR for HCMV UL55 gene. HCMV UL55 PCR amplified products are identified in a representative agarose gel at 140 bp from specimens derived from human colon cancer. Numbers above lanes refer to patient biopsy specimens in Table 4. Most specimens had 2-3 DNA elutions made for each, and in some tumor samples amplified products were identified in only one or two samples from a particular tumor. HCMV UL55 DNA amplimers are visible in several tumor samples (e.g., 2c, 27b, 6, 20, and 29a), but not in non-neoplastic adjacent tissues from tumor patients (eg., 2a, 24b, 29b). Multiple blank paraffin block specimens (b) that were processed identically as tumor samples are negative, as are multiple negative PCR water controls (w). M=DNA ladder lane.

To confirm that the ISH probe was specific for HCMV nucleic acids, DNA was extracted from paraffin sections of several of the tumors (and adjacent non-neoplastic colonic epithelium specimens) that were positive for HCMV by IHC. DNA extracted from the patient samples (and an equivalent volume of DNA buffer from identically processed blank paraffin control specimens) was subjected to nested PCR using PCR primers specific to 140 bp region of the HCMV glycoprotein B (UL55) gene. Amplified UL55 PCR products were detected in at least one elution tube from 6/6 tumors (5 adenocarcinomas and one polyp) that were immunoreactive for HCMV, but in none (0/3) of the non-neoplastic tumor-free margin biopsy samples from 3 of these same patients (FIG. 11). No HCMV amplified products were detected in any (0/5) of the blank paraffin block control samples or PCR water negative controls (0/4) that were run in the same nested PCR reaction. Amplified PCR products from all 6 tumor cases were cut from agarose gels, and the DNA was extracted and submitted for direct DNA sequencing. DNA sequencing of these amplified PCR products indicated that all 6 were the HCMV UL55 gene.

The cyclooxygenase-2 (COX-2) enzyme is thought to play an important role in the development and malignant progression of human colorectal cancer (Williams et al. 1999 Ann N.Y. Acad. Sci.889:72-83). Since COX-2 "iRNA expression is induced in human cells after infection with HCMV (Zhu et al. 1998 Proc Natl Acad Sci USA 95:14470-5) and is required for HCMV replication (Zhu et al. 2002 Proc Natl Acad Sci USA, published as electronic report prior to publication), COX-2 IHC was performed on several tumor specimens to determine if COX-2 localization correlated with HCMV protein expression. COX-2 expression was detected in regions of tumor epithelium that corresponded to areas of IE1-72 and pp65 immunoreactivity, while little COX-2 immunoreactivity was detected in normal appearing colonic epithelium except in inflammatory cells (FIG. 10, panels S and T).

Figure 12:
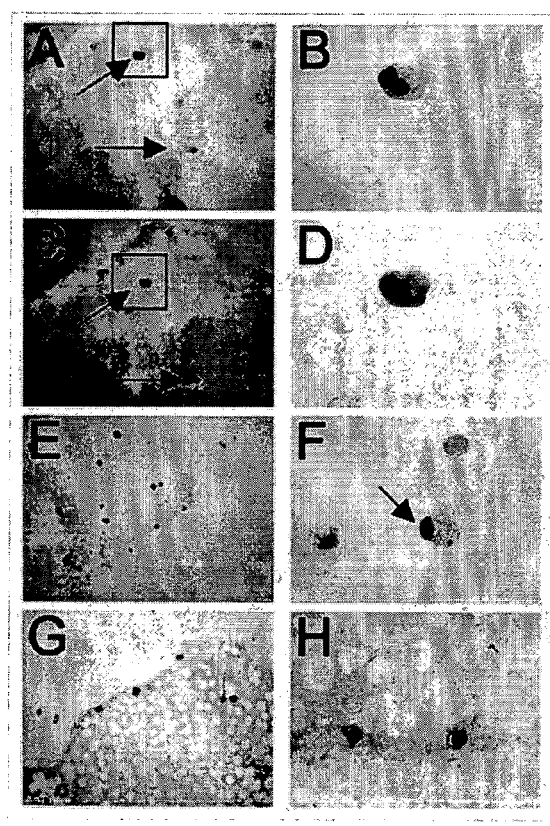
FIG. 12 shows double-staining immunohistochemistry and in situ hybridization for HCMV in caco-2 colon adenocarcinoma cells. In panel A, rare caco-2 cell nuclear immunoreactivity (black staining identified by arrows) for HCMV IE1-72 is seen in a colony of caco-2 cells (boxed cell in A is seen at high power in panel B). In panel C, after double labeling with mAb for COX-2, HCMV-infected cells specifically show increased COX-2 expression (arrows illustrate same cells shown in panel A, with increased COX-2 expression—red chromogen). Panel D shows high power view of double-labeled IE1-72 (black) and COX-2 (red) caco-2 cell from panel C, with no immunoreactivity seen in uninfected cells in background. Panels E and F show Low (E) and high (F) power views of a colony of caco-2 cells double-stained with a mAb for IE1-72 (brown chromogen in nuclei) and Bcl-2 (red chromogen in cytoplasm). In situ hybridization of HCMV-infected cells at low (panel G) and high (panel H) power with probe specific for HCMV immediate early gene mRNA shows discreet hybridization pattern of infected cells similar to that found with IE1-72 immunostaining. Original magnification×40 (panels A, C, E, G) and ×400 (panels B, D, F, H).

HCMV infection led to COX-2 expression in infected cells. The caco-2 human colon epithelial adenocarcinoma cell line, which has been extensively studied with respect to both COX-2 expression and HCMV infection (Jarvis et al 1999 J Virol 73:4552; Tsujii et al. 1997 Proc Natl Acad Sci USA 94:3336), was infected in vitro with HCMV. In culture, caco-2 cells arrest in the G1 stage of the cell cycle after cell division, and therefore only a small percentage of cells can typically become infected with HCMV (at moi 1-5 pfu/cell) (Jarvis 1999). Caco-2 cells were infected with HCMV Towne strain (moi 1-5), and IHC analysis was performed for HCMV with anti-IE1-72 mAb using a peroxidase detection system with a black chromogen (FIG. 12 panels A and B). These colonies were photographed, and IHC performed on the same cells with anti-COX-2 mAb, using an alkaline phosphatase detection system with a red chromogen. Anti-IE1-72 nuclear immunoreactivity was clearly observed in rare caco-2 cells at 48 hours after infection, often in multinucleated giant cells. Double-labeling with anti-COX-2 monoclonal antibody revealed intense COX-2 expression only in cells immunoreactive for IE1-72 (FIG. 12 panels C and D). No IE1-72 immunoreactivity was observed, and only faint COX-2 immunoreactivity was observed in control (mock infected) caco-2 cells.

Expression of Bc1-2 in colorectal adenocarcinoma is thought to play an important role in early tumor progression and may be activated through COX-2 expression. The IHC double-labeling experiments were repeated with the antibody to IE1-72 (using a brown chromogen) followed by an antibody for Bc1-2 (using a red chromogen). Like COX-2, Bc1-2 is known to be induced in HCMV-infected cells and can confer upon these cells resistance to chemotherapeutic agents. Expression of Bc1-2 in colorectal adenocarcinoma is also thought to play an important role in tumor progression. We found that caco-2 cells expressing IE1-72 also had increased expression of Bc1-2, which was not observed in the uninfected adjacent cells or mock infected cells (FIG. 12 panels E and F).

ISH using the biotinylated oligonucleotide probe specific for HCMV mRNA corroborated the IHC results, revealing hybridization of HCVM nucleic acids in rare caco-2 cells. No evidence of HCMV nucleic acid hybridization was observed in mock infected control cells, or in HCMV-infected caco-2 cells in which the probe was omitted from the hybridization reaction.

These data are the first to show the presence of HCMV proteins and nucleic acids in a high percentage of human colorectal adenocarcinoma specimens in humans. Current paradigms for the development of human colorectal adenocarcinoma indicate that a multi-step progression of genetic mutations occurs over years, characterized by the progression from polyp to invasive adenocarcinoma. Key among these alterations are those that dysregulate the adenomatous polypi coli (APC) and p53 pathways and activate the Bc1-2 and COX-2 prostaglandin synthesis pathway. The findings in the present disclosure are unexpected yet could tie in with existing paradigms. As discussed above HCMV is present in 50-90% of the adult population, can persistently infect colon epithelium, can synergize with other carcinogens to induce DNA mutations, can inhibit apoptosis, and can induce COX-2 and Bc1-2 expression. Induction of COX-2 and Bc1-2 expression by HCMV in colon adenocarcinoma cells in vivo, as shown in caco-2 cells, could enhance the malignant phenotype of these cells. In addition, HCMV is known to dysregulate a wide array of potentially important oncogenic pathways, including those affecting apoptosis, cell cycle, mutagenesis, angiogenesis, invasion and immune evasion. It is postulated that colonic epithelial cell with a prior DNA "hit" could acquire alterations in cell cycle control mechanisms that allow it to become persistently infected by HCMV, thereby inhibiting apoptosis. Prolonged permissive infection, in conjunction with HCMV's ability to promote immune evasion might allow such an infected cell to acquire multiple mutations leading to dysregulated clonal expansion. HCMV induced inactivation of APC and p53 function and upregulation of COX-2 and Bc1-2 might further enhance the ability of these cells to overcome selective pressures against malignant progression. Finally, a loss of HCMV in poorly differentiated adenocarcinomas may ensue if fully transformed cells lose selective advantage for retaining HCMV, as has been hypothesized in the "hit and run" HCMV oncogenic transformation paradigm.

Methods

Immunohistochemistry. Immunohistochemistry is performed as described herein. Slides were incubated with appropriate antibody as follows or as described above: anti-IE1-72 (1:20-25, BioGenex®), anti-pp65 (1:30-40, Novocastra®), anti-p52/76 kD (1:30, Novocastra®), anti-CD34 (1:15-25, BioGenex®) and anti-COX-2 mAb (1-30, Cayman Chemical®) or no antibody.

In vitro immunohistochemistry experiments were performed as described herein. Slides were incubated with appropriate antibody as follows or as described above: IE1-72 (1:200; BioGenex®), GFAP (1:800; BioGenex®), or neurofilament (1:600; Innovex®). Detection of mAb was performed with an HRP system (FIG. 6, h-p; chromogen DAB) and an AP system (FIG. 6, a-c; chromogen nuclear fast red). Slides were counterstained with hematoxylin.

In situ hybridization. In situ hybridization was performed as described above. In some experiments described above, a biotinylated 21 base oligonucleotide specific for HCMV early gene mRNA 5'-GTGGTGGCGCTGGGGGTGGCG-3' (SEQ ID NO. 11) and biotinylated probe positive (for poly-A mRNA) and negative control (for HSV-1/2) probes were obtained (Winklhofer et al. 2000. Virology 275:323, ResGen) and used for detection of HCMV mRNA.

In some experiments described herein, a digoxigenin labeled HCMV total genome DNA probe was used (Zymed Labs) to detect HCMV DNA. Positive (for endogenous alu DNA sequence) and negative (nonspecific DNA) digoxigenin-labeled control probes were provided.

Double labeling of paraffin sections for HCMV DNA and GFAP protein. ISH for HCMV DNA was performed as described herein. Citra antigen retrieval (BioGenex®), endogenous peroxidases block (3% $H_2O_2$, 12 min), and FC Receptor Block (Innovex®) treatments were performed, followed by incubation with anti-GFAP polyclonal antibody (Zymed® Labs, 2 hr, 20° C.). GFAP was detected with a multi-link AP detection system (BioGenex®) and NBT chromogen.

RT-PCR, PCR, and DNA sequencing of PCR products. For frozen specimens, total RNA was purified from appropriate samples (obtained with appropriate approvals) using RNA STAT-60 (Tel-Test 'B', Inc.). One microgram of RNA was reverse-transcribed using MuLV Reverse Transcriptase (Applied Biosystems®) at 42° C. for 15 min. For paraffin embedded samples, DNA was purified from a subset of the specimens using DNeasy Tissue System (Qiagen®) as per manufacturer's instructions. For each specimen, at least 2 tubes of DNA were eluted and run as separate samples for PCR. From each sample approximately 250 ng of DNA was amplified by using nested primers.

PCR amplification of the cDNA was performed with primers specific for the HCMV UL83 (pp65) gene (ResGen). DNA from HCMV strain AD169-infected HFF cells was a positive control. Samples were amplified (40 cycles; 94° C./1 min, 69° C./1 min, 72° C./1 min) with a final extension at 72° C./10min, and DNA was resolved on 2% agarose gel stained with ethidium bromide. This reaction was repeated without RT to confirm that PCR products were derived from RNA. To confirm the presence of RNA in all samples, the exact RT-PCR reaction was repeated with primers to GAPDH.

For PCR of UL73, samples were amplified with primers to UL73 (forward 5'-ggatccgctagcatggagtggaacacac-3'; reverse 5'-tctagatcaatagcctttgg-3') and resolved on agarose gel and sequenced as described above.

For PCR of UL55 (gB), nested PCR using internal and external primers specific for UL55 were used as previously described (Kuhn et al. 1995 J Med Virol 47:70). DNA was resolved on a 1.5% agarose gel.

For some samples, PCR products were excised from the gels (gel extraction kit, Qiagen®) and analyzed by automated sequencing (ABI Model 377 DNA Sequencer). For other samples, PCR products were cloned into appropriate vectors, such as pCR2.1-TOPO (Invitrogen®), according to instructions. Clones were multiplied and analyzed by automated sequencing (ABI Model 377 DNA Sequencer). The sequences were then subject to identification with an NCBI BLAST search.

Electron microscopy immunohistochemistry (EM-IHC). GBM tissues were obtained at surgery (with appropriate approvals) and prepared for EM-IHC with anti-pp65 mAb (Novocastra®) as described (Del Valle et al. 2001. Cancer Res. 61:4287). Secondary antibodies bound to 35 nm gold particles (Electron Microscopy Sciences) were used for visualization.

Glioblastoma specimen preparation and cell culture. Fresh GBM specimens from 3 patients were obtained at surgery and either dispersed into a single cell suspension (specimen #1) or homogenized into a cell-free suspension in saline (specimens #2 and #3). 50 µl of these specimens were plated onto confluent primary human foreskin fibroblasts (HFF) (in DMEM, 10% fetal bovine serum) in culture. Untreated HFF cells were negative controls. HFF plates (at 80% confluence) infected with a clinical strain of HCMV (isolated by W. J. B.) were positive controls. Plates were incubated for 3 weeks, and subjected to IHC and ISH analysis as described.

Infection of caco-2 cells in vitro and immunohistochemistry and in situ hybridization. Human colon epithelial derived caco-2 cells were obtained from the American Type Culture Collection (ATCC®, Rockville, Md.) and cultured at 37° C. in 5% $CO_2$ in DMEM with 10% fetal bovine serum (FBS, BioWhittaker®, Walkersville, Md.). Caco-2 monolayers were grown for 5 days in culture, at which time they had assumed characteristic colony formation. Cells for HCMV infection (and mock infection) were washed with PBS, and infected (or mock infected) with HCMV Towne strain (obtained from ATCC®) by addition of virus to the media at a multiplicity of infection (moi) of 1 in DMEM with 20% FBS. After addition of virus, infection was allowed to proceed for 1 h at 37° C. Cells were then washed with PBS and DMEM with 10% FBS was again added in an environment of 5% $CO_2$ at 37° C. After 48 h, cells were fixed with methanol (-20° C., 20 min.), air-dried and processed for double-staining immunohistochemistry (DSIHC) or in situ hybridization (ISH). For DSIHC, cells were rinsed with TBS (pH 7.6), blocked for endogenous peroxidase (3% $H_2O_2$, 8 min.), and then incubated in FC Receptor Block (BioGenex®, 20° C., 10 min.). Slides were blotted dry and primary mAb to IE1-72 (1:300; BioGenex®) was added (4° C., 12 h). Slides were rinsed with TBS and detected with a 3-step HRP system (BioGenex®) using DAB black chromogen (Zymed® Labs) or DAB brown (Innovex® Sciences) and cover slipped with an aqueous mounting media. Slides were photographed and then soaked in water to remove cover slips and mounting media. For COX-2 double-staining, to the IE1-72-DAB black immunostained cells, a mAb to COX-2 (1:200, BioGenex®) was added (4° C., 12 h) and detected with three-step alkaline phosphatase system using fast red chromogen (BioGenex®). For Bcl-2 double-staining, to the IE1-72 DAB brown immunostained cells, a mAb to Bcl-2 (Novocastra®, 1:200) was added (4° C., 12 h) and detected with three-step alkaline phosphatase system with fast red chromogen as above. DSIHC slides were then photographed again after mounting with aqueous media and cover slipping. For ISH of HCMV-infected caco-2 cells in vitro, cells were infected as described above and then fixed in methanol (-20° C., 20 min.) and then air-dried. Biotinylated CMV probe or control probe was added as described above. Cover slips were added and cells were denatured (90° C., 15 min.), and then hybridized (37° C., 90 min.) in a humidified chamber. Cells were then soaked in TBS and then probe wash (BioGenex®) was added for 10 min. and hybridization was detected as described above with the chromogen NBT. Cells were mounted, cover slipped and photographed.

EXAMPLES

Example 1

Immunohistochemistry for CMV Detection in Paraffin Sections

Specimen Preparation

Desired tissue specimens embedded in paraffin blocks are prepared according to standard techniques known in the art. Paraffin blocks are cut to a thickness of 4-6 microns. In one embodiment, for glioblastomas, paraffin blocks are cut to a thickness of 6 microns. In an alternate embodiment for breast, prostate, colon, cervix, and ovary paraffin blocks may be cut to a thickness of 4-5 microns (Table 5). The thickness of the slices may be varied beyond the ranges discussed above, as may be determined by one of ordinary skill in the art.

Paraffin sections are spread by floating in distilled or deionized water and placed on slides. Histology additives such as gelatin, stay-on, or other similar protein additives may be used, but may cause increased non-specific or background staining. In one embodiment, Plus Slides or equivalent Superfrost Fisher 12-550-15 are used. Other slide types may be used provided that the sections adhere to the slide during the enzyme digestion and antigen retrieval steps below.

Paraffin sections are allowed to air dry at room temperature for at least one hour by placing paraffin sections on a paper towel or similar absorbent material. Paraffin sections are further dried in a heated oven for at least 4 hours. In one embodiment, incubation is carried out in a 50° C. oven for 4 hours. In an alternative embodiment paraffin sections are incubated in a 50° C. oven overnight.

The sections are then de-paraffinized. In one embodiment, the sections are de-paraffinized by incubating the paraffin sections in xylene. The xylene used may be reagent grade or ACS grade, or other grade of similar purity. In one embodiment, the xylene incubation is for at least 30 minutes in a 50° C. oven. In an alternate embodiment, xylene incubation may be carried out overnight at room temperature. Other incubation times and methods may also be used as would be recognized by one of ordinary skill in the art. After the xylene incubation, sections are rinsed by dipping/rinsing in xylene. In one embodiment, the sections are dipped in xylene at least 20 times at room temperature. This procedure may be repeated at least one time. Sections are then rinsed by dipping/rinsing in ethanol solutions (reagent grade) of decreasing concentration at room temperature. In one embodiment, the sections are dipped in the appropriate ethanol solutions at least 20 times at room temperature. In one embodiment, the following ethanol concentrations are used: 100% (1×); 95% (1×); 75% (1×); and 50% (2×). Alternate schemes for ethanol washes may be used, including, but not limited to, the use of different ethanol gradients and increasing the number of washes at each step.

After ethanol washes, the sections are rinsed in running water. Sections are transferred into a tris-buffered saline (TBS) solution, pH.7.6 (Sigma Chemical Company, catalogue number T4253). Detergent may be added to TBS to help reduce the surface tension of the liquid. In one embodiment, 3 drops of Triton-X (Sigma Chemical Company) are added per liter of TBS (TBST). Sections may be stored in TBST for extended period of time (not to exceed 3 weeks) 2-8° C., or at room temp for 8 hours.

Post-Fixation Epitope Conditioning

The assay conditions are optimized to take into account the variability that occurs in the original fixation step via epitope conditioning. The fixation method used, the age of the samples and other factors may effect the sensitivity of detection in the assay. A post-fixation step may be used to take this variability into account.

After incubation in TBS or TBST, pH 7.6 samples may be post-fixed as described below. The post-fixation step eliminates substantial variability that may be present in the samples. This variability may be the result of the variability in fixation with the sample itself, autolysis of the sample, age of the sample and the depth of the sample within the paraffin section (as described above).

Samples are post-fixed by incubation with 10% neutral buffered formalin (NBF) at room temperature. The duration of the post-fixation step is sufficient to provide sufficient time for epitope conditioning. In one embodiment, the duration of the post-fixation step is determined by the age of the tissue fixed in paraffin from which the sample is obtained. For tissues one month old or less, post fixation times of 15-20 minutes are appropriate. For tissues 2-6 months old, post fixation times of 45-60 minutes are appropriate. For tissues 0.5-2 years old, post fixation times of 1.5-2 hours are appropriate. For tissues 2-4 years old, post fixation times of 3-4 hours are appropriate. For tissues over 4 years old, post fixation times of 4-6 hours are appropriate. After post-fixation, samples are washed in TBS or TBST, pH 7.6.

Samples are then subject to enzyme digestion. The particular enzyme used may be determined based on the sample examined (type of tissues), the age of the sample and the primary antibody to be used. In one embodiment, the samples are incubated with Pepsin (Biogenex® Laboratories) at 37° C. for 4-6 minutes. In an alternate embodiment, Trypsin may be used (Biogenex® at 37° C. for 4-6 minutes). Other enzymes may also be used to provide similar results as may be determined by one of ordinary skill in the art given the teachings of this disclosure. A list of exemplary tissue types examined, primary antibodies employed and enzymes used is given in Table 6. After enzyme incubation, samples are quickly rinsed in distilled water and transferred to TBST buffer, pH 7.6.

Antigen Retrieval

After enzyme incubation, samples are subject to an antigen retrieval step. The buffer used in the antigen retrieval step may be varied depending on the fixative used in the initial preparation. In one embodiment, for formalin fixed tissues, antigen retrieval is carried out by incubation in citra-buffer (Epitope Recovery/Dialize buffer also known as Citra buffer), pH 7.6. In one embodiment, the citra buffer is pre-warmed to 85-90° C. Samples are immersed in pre-warmed citra buffer and transferred to a water bath (45-50° C.). In one embodiment, samples are incubated in the water bath for 2-2.5 hours, although other incubation times may be used. Slides are allowed to cool down at room temperature for 5 min, then rinsed with running deionized water for 2 minutes then transferred to TBST (pH 7.4). For samples originally fixed with fixatives other than formalin, distilled water is used in place of citra buffer in the antigen retrieval step.

After antigen retrieval, the samples may be treated with one or more of the various blocking agents as described below. Samples may be treated to inactivate endogenous peroxidases by incubation in 3% $H_2O_2$ (reagent grade) for 12 minutes at room temperature. Samples are quickly rinsed in distilled water and transferred to TBST.

The sample may also be blocked with a protein blocking reagent, such as FC Receptor Block. The samples are circled with a PAP Pen and a sufficient volume of FC Receptor Block (Innovex® Biosciences, Richmond, Calif.) is added to cover the sample. Incubation is carried out for 15-20 minutes at room temperature. In an alternate embodiment, Background Blocker (BB) (Innovex®, Richmond Calif.) may be used in place of FC Receptor Block. After incubation, the samples are blotted to remove a substantial amount of the solution, but samples are not allowed to dry.

Samples may also be blocked with avidin/biotin solution to block any endogenous biotin moieties that may be present in the sample (Biogenex® or Dako® Corp.). A list of exemplary optimal blocking solutions for different sample types and primary antibodies is given in Table 6.

It is preferred that the assay conditions (including but not limited to, epitope conditioning, enzyme digestion, antigen retrieval and blocking methods) be optimized such that the samples yield no, or substantially no, background after incubation with the detection system only (by omitting the primary antibody). Certain optimal conditions are provided in Table 7 as exemplary conditions. Further optimization is well within the ordinary skill in the art when guided by the teachings of the present disclosure.

Example 2

Antibody Incubation and Development

Samples are now ready for addition of antibody. For assay optimization, the primary antibody is omitted (as discussed above). Samples are incubated with TBST, pH 7.6 (containing no primary antibody) overnight at 2-8° C. After incubation, samples are quickly rinsed in TBST and transferred to fresh TBST buffer. For detection, primary antibodies are added as appropriate. The primary antibodies are added in an appropriate volume of diluent so that the sample is completely covered. Any primary antibody that is specific for HCMV may be used, including but not limited to IE1, IE2, PP65 and HCMV Late Ag. In one embodiment, Common Antibody Diluent (Biogenix Laboratories) is used. In one embodiment, all antibodies are diluted fresh and use immediately or no more than 24 hours after dilution. Incubation is continued overnight in humidified container at 4-8° C. Antibody concentrations may be adjusted from lot to lot of antibody due to variations from lot to lot. A list of antibody commercial sources and dilutions for use in the immunohistochemistry protocol is given in Table 7 as a reference. After incubation with primary antibody, the slides are washed in TBST or TBS. In one embodiment, the wash is 3×3 min. at room temp. or overnight at 2-8° C. Slides are then blotted dry and secondary antibody is applied.

Signal detection reagents are then added to the samples. In one embodiment, the signal detection reagents are secondary antibodies, a labeling reagent and chromophores suitable for use with the labeling reagent. The labeling reagent may be directly conjugated to the secondary antibody. The labeling reagent may be an enzyme, a radioisotope, a fluorescent reagent, a luminescent reagent or a chemiluminescent reagent. In one embodiment, monoclonal antibody is used as the secondary antibody (Biogenex®). For monoclonal antibodies as the secondary antibodies, a dilution of (1:20) is used and incubation carried out at room temperature for a period of time sufficient to permit secondary antibody binding. In one embodiment, this period of time is 30-45 minutes. The monoclonal antibody may be modified for use in the detection steps below. In one embodiment, the secondary antibody is biotinylated. In alternate embodiments polyclonal antibody, or other suitable antibody fragments, may be used. After incubation with secondary antibody, the samples are rinsed TBS or TBST. In one embodiment, the samples are rinsed 3× at room temperature to remove unbound secondary antibody. Samples are then incubated with appropriate reagents for detection. In one embodiment, a 3-stage horseradish peroxidase (HRP) detection system (BioGenex®, Dako®, & Innovex®) is used. The peroxidase enzyme may be in the form of a peroxidase-labeled streptavidin if the secondary antibody is biotinylated. The peroxidase enzyme is incubated at room temperature for an amount of time sufficient to allow the streptavidin to bind the biotinylated secondary antibody. In one embodiment, this period of time is 30-45 minutes. Samples are rinsed with TBS or TBST to remove unbound reagents. Chomophore substrates suitable for use with peroxidase enzymes are then added to the samples for development.

In one embodiment, diamino benzidine (DAB) (Innovex® Biosciences) is used. The substrates are incubated for 1-5 minutes until a suitable level of visualization is obtained. Visualization may be monitored by microscopic evaluation. Once a desired level of development is obtained, the samples are transferred to tap water to stop further development of the substrate. In one embodiment, a tyramide based peroxidase signal amplification to enhance detection (Dako®) may also be used. Other development systems utilizing different enzymes and substrates may be used as may be determined by one of ordinary skill in the art.

The samples may then then counterstained with Harris hematoxylin as per standard procedures by dipping samples 5 times or more depending on intensity of counterstain desired. The samples are rinsed in running tap water. Excess hematoxylin is removed by dipping in bluing solution 5-10 times. The samples are rinsed in running tap water.

The samples are dehydrated in descending series of alcohol washes by dipping the samples 10× each in each concentration of alcohol. In one embodiment, ethanol (reagent grade) is used and the concentration ranges from 50-100%. For example, samples may be subjected to alchol washes of 50% (1×), 75% (1×), 95% (1×), and 100% (2×). The samples are then washed with xylene by dipping (10×). The xylene was may be repeated as desired. In one embodiment, 2 xylene (reagent grade) washes are used. A cover slip is added to the slides and mounted with permount or similar material.

Figure 13:
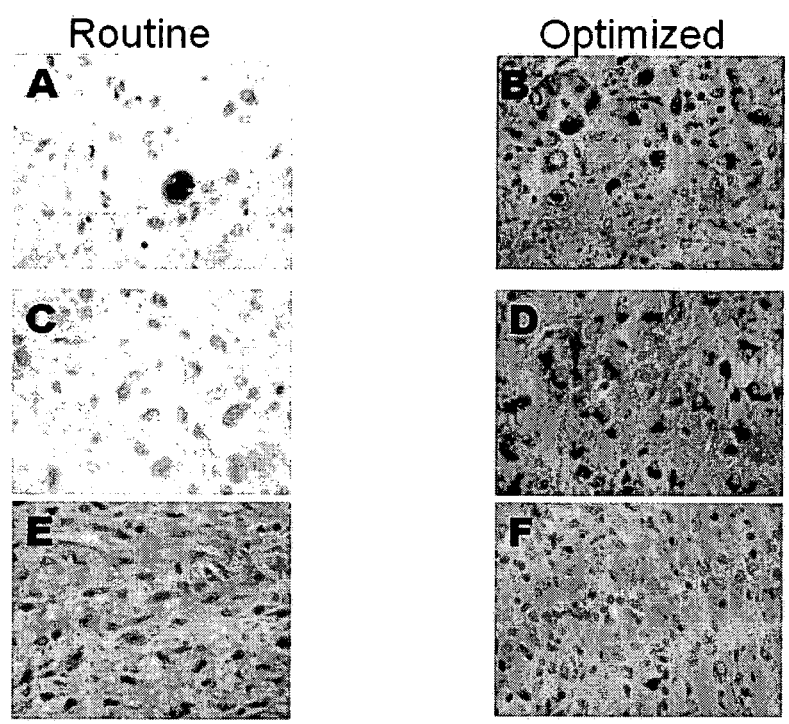
FIG. 13 shows comparison of the prior art immunohistochemistry method and the immunohistochemistry method of the prior disclosure. HCMV infected lung tissue and glioblastoma tumors were subject to immunohistochemistry to detect HCMV by the prior art method (labeled routine, panels A, C and E) or the method of the instant disclosure (labeled optimized, panels B, D and F). Primary antibody to IE1 was used for all samples. Brown staining indicates IE1 immunoreactivity.

The immunohistochemistry method presented above offers increased sensitivity as compared to previous methods used in the art. A comparison was conducted to illustrate this difference (FIG. 13). Paraffin sections obtained from HCMV infected lung (panels A and B) and glioblastoma tumors (panels C-F) were immunostained for HCMV using anti-IE1 antibody. Two methods were used: 1) the prior art method as described by the antibody manufacturers (labeled as routine, panels A, C, and D) and the method of the instant disclosure (labeled as optimized, panels B, D, and F) (FIG. 13). As can be clearly seen, the optimized protocol produced superior detection of HCMV in lung and glioblastoma tumor samples. For instance, while only very minimal brown staining is evident in the "routine" immunostain for CMV of the glioblastoma in FIG. 13, panel C, intense brown staining is evident in another section from the same specimen (FIG. 13, panel D) using the same antibody after incorporation of the optimized detection techniques we describe above.

Example 3

In Situ Hybridization for CMV Detection in Paraffin Sections

Paraffin sections are prepared on glass slides as per the immunohistochemistry protocol above. Once paraffin sections are mounted on slides, the sections are deparaffinized using xylene and graded alcohols as described in the immunohistochemistry protocol above. However, whenever water is specified in this protocol, it is understood that the water is DNAse and/or RNAse free and may contain DNAse and/or RNAse inhibitors (RNAse inhibitor, Biogenex®) After hydration, post-fixation epitope conditioning (as described in the immunohistochemistry techniques above) may be preformed.

Samples are then subject to enzyme digestion. The particular enzyme used may be determined based on the sample examined (type of tissues), the age of the sample and the primary antibody to be used. In one embodiment, the samples are incubated with Pepsin (Biogenex® Laboratories) in 0.1 N HCL at 37° C. in a thermocycler (Misha Thermocycler™, Shandon Lipshaw). The incubation time may be dependent on the type of tumor examined. For example, in brain tissue, low grade tumors and normal brain are incubated with pepsin for 20 minutes, while high grade tumors are incubated for 30 minutes. Optimization of the incubation time is within the ordinary skill in the art given the teachings and guidance of the instant specification. Other enzymes may also be used to provide similar results as may be determined by one of ordinary skill in the art. The samples are rinsed with deionized water. Alternatively, low temperature antigen retrieval with citra buffer (overnight at 37° C.) can be used instead of enzyme digestion if enzyme digestion does not yield desired signal, ie., the signal is not clean or tissues are over digested. The samples are then dehydrated with grade alcohols as described in the immunohistochemistry protocol up to 100% alcohol.

The appropriate nucleic acid probes are added to the samples in hybridization buffer provided by the manufacturer of the probe. The probes used may be any nucleic acid molecule that is capable of binding to a portion of the nucleic acid encoding HCMV. Some of these nucleic acid probes are described in the instant specification. Preferably, the probe will bind specifically to the nucleic acid encoding HCMV. The nucleic acid probes may be labeled with biotin or fluorescein for RNA or DNA detection. A cover slip is added to the samples. The samples are subject to nucleic acid denaturation by incubation in a thermocycler (Misha Thermocycler) at 90° C. The incubation time may be dependent on the type of tumor examined. For example, in brain tissue, low grade tumors and normal brain are incubated for 10 minutes, while high grade tumors are incubated for 15 minutes. Optimization of the incubation time is within the ordinary skill in the art given the teachings and guidance of the instant specification. After denaturation, the samples are then hybridized with the probe by incubation overnight in humidified chamber at 37° C.

After incubation, the samples are soaked in TBS or TBST pH 7.6 until cover slips float off. The samples are subject to a stringency wash at 40° C. for 20 minutes. In one embodiment, the stringency wash comprises SSC buffer (Biogenex®). The degree of stringency provided during the stringency washed may be altered by changing the solutions used during the stringency wash, changing the incubation time and/or changing the temperature of incubation. Such modifications to achieve the desired signal to noise ratio are within the ordinary skill in the art given the teachings of the instant disclosure. The samples are rinsed with TBST, pH 7.6. The wash may be repeated as desired. The samples may be subject to a hybridization wash buffer (Biogenex®) for 10 minutes at room temperature. The samples are rinsed with TBST, pH 7.6. The wash may be repeated as desired. The samples are protein blocked as per standard protocols for 15 minutes at room temperature. In one embodiment, FC Receptor Block is used as the blocking agent.

The samples are the subject to appropriate detection steps. As discussed above the nucleic acid probes may be tagged with biotin or fluorescein, enabling detection of the nucleic acid molecules by immunohistochemistry techniques. The detection steps include attaching a reporter group to the tagged nucleic acid molecules. The attachment may be indirect or direct. In one embodiment an indirect detection method is used. In this embodiment, a mouse anti-biotin or mouse anti-fluorescein is incubated with the sample for thirty minutes at room temperature. The sample is washed 3×3 minutes in TBST pH 7.6. The sample is incubated with a biotinylated goat anti-mouse $FAB_2$ fragment secondary antibody for thirty minutes at room temperature. The sample is washed 3×3 minutes in TBST pH 7.6. The sample is then incubated with alkaline phosphatase-streptavidin label for 30 minutes at room temperature. The sample is washed 3×3 minutes in TBST pH 7.6. The appropriate substrate is added as per standard protocols and incubated for 5 minutes at room temperature. In one embodiment, nucleic acid probe was detected using DNA/mRNA alkaline phosphatase supersensitive detection system (BioGenex®, chromogen nitro-blue tetrazolium, NBT) as per manufacturer's instructions. The reaction is stopped at the desired intensity of signal (about 5 minutes) with distilled water. The samples may be the counterstained with nuclear fast red or methyl green or eosin as desired as per standard procedures. The samples are rinsed in running tap water. The slides are then mounted as per standard procedures for the appropriate chromogen.

Example 4

RNA in Situ Hybridization for CMV Detection in Cells In Vitro

Appropriate cells selected for study are grown in culture as desired and mounted to slides as per standard procedures. The slides are rinse with distilled, deionized water. Whenever water is specified in this protocol, it is understood that the water is DNAse and/or RNAse free and may contain DNAse and/or RNAse inhibitors. The slides are fixed in methanol at −20° C. for 20 minutes. The slides are allowed to air dry. Suitable nucleic acid probes are added as described above in reference to paraffin sections.

The samples are subject to nucleic acid denaturation by incubation in a thermocycler (Misha Thermocycler) at 90° C. The incubation time may be dependent on the type of tumor examined. In one embodiment, the cells are denatured for 5-15 minutes. Optimization of the incubation time is within the ordinary skill in the art given the teachings and guidance of the instant specification. After denaturation, the samples are hybridized with probe by incubation for 1 to 1.5 hours in humidified chamber at 37° C.

After incubation, the samples are processed for detection as described above for paraffin sections.

Example 5

Immunohistochemical Determination of HCMV by a Kit Method

The kit is designed to specifically localize low copy numbers of HCMV epitopes in human tumors that cannot be detected by currently available detection systems. The detection/localization kit is suitable for tissue culture cells, frozen sections, cytology smears and for paraffin embedded patient tissue samples.

The kit may contain one or more of the components listed below as desired. Other components may also be included.
Component 1: Epitope conditioning reagents (bottles 1-3, 12-13)
  Bottle 1—10% buffered formalin in TBST
  Bottle 2—penfix (tissue conditioner 2)
  Bottle 3—distilled water (tissue conditioner 3)
  Bottle 12A—Diluent for pepsin
  Bottle 12B—Diluent for trypsin Bottle 13A—Pepsin
Bottle 13B—Trypsin
Component 2: Antigen recovery reagents (bottles 4-5)
  Bottle 4—citra retrieval buffer
  Bottle 5—distilled water
Component 3: Control Tissues
  Positive Control HCMV tissues
  Negative Control HCMV tissues
Component 4: Primary antibodies specific for HCMV (bottles 7-9). The primary antibodies described below are exemplary only, it being understood that any antibody reactive with HCMV may be used.
  Bottle 6—CMV IE1/IE2
  Bottle 7—CMV cocktail antigens
  Bottle 8—CMV Late Antigen
  Bottle 9—Common Antibody Diluent (Biogenix)
Component 5: Secondary antibody/Signal Generating Reagents (bottles 10-11, 16-18). The secondary antibodies described below are exemplary only, it being understood that a variety of secondary antibodies and labels may be used.
  Bottle 10—Secondary antibody (biotinylated) against primary antibody used
  Bottle 11—Streptavidin Horseradish Peroxidase labeling reagent
  Bottle 16—detection substrate, such as Diaminobenzidine chromogen
  Bottle 17—Chromogen enhancer
  Bottle 18—Hematoxylin counterstain
Component 6: Supplementary reagents (bottles 14-15, 19-20)
  Bottle 14 Tris buffer solution with triton X
  Bottle 15A—Fc receptor block
  Bottle 15B—30% hydrogen peroxide stock
  Bottle 15C—Avidin Block
  Bottle 15D—Biotin Block
  Bottle 19—Aqueous mounting medium
  Bottle 20—Permanent mounting medium
Component 7: Negative control antibodies (bottles 20-21).
  The negative control antibodies described below are exemplary only, it being understood that a variety of isotype matched negative control antibodies may be used.
  Bottle 20—Cd34 antibody as Igg1 negative control
  Bottle 21—Smooth Muscle Actin as IgG2a negative control The protocol used in the kit as described herein follows the procedures described previously. For clarity, the procedure has been simplified and references to previous sections of this disclosure are made to reference specific steps as required. A tissue sample is obtained from a subject in need of HCMV testing. The sample is fixed according to standard protocols (such as with 10% NBF) and encased in paraffin as per procedures known in the art. For the purpose of this example, assume the tissue sample is derived from the breast of said patient and the tissues sample is fixed with formalin. Paraffin sections (the number of which are determined by the number of primary antibodies to be used) are cut to a thickness of approximately 4 microns in a water bath and placed on Plus Slides or equivalent as described in the immunohistochemistry section in the specification. The slide may be supplied with the kit. Paraffin sections are allowed to air dry at room temperature, followed by incubation in a 50° C. oven for 4 hours.

The sections are deparaffinized by incubation in xylene (reagent grade) for 30 minutes at 50° C. and are dehydrated as described in Example 1. The samples are rinsed in running water for 1 minute and placed in TBST buffer (pH 7.6). The TBST (component 6, bottle 14) may be supplied with the kit. The TBST solution may be supplied as a stock with directions for preparation. The samples are then conditioned by incubation with appropriate epitope conditioner (10% NBF) as described in Example 1. The 10% NBF solution may be supplied in component 1, bottle 1. Component 1 will also contain "tissue conditioner 2" in bottle 2 (pen/fix), and "tissue conditioner 3" in bottle 3 (distilled water). The samples are enzyme digested (pepsin, bottle 13A and trypsin, bottle 13B). Enzyme digestion is performed as per directions on the container by reconstituting the enzyme in appropriate buffer (bottles 12A and 12B) and incubating for 4-6 minutes at 37° C. as described in Example 1. After enzyme digestion, samples are subject to antigen recovery as described in Example 1 using the appropriate antigen recovery reagents (bottles 4, citra buffer and bottle 5, distilled water). After epitope recovery, the samples are washed with deionized water and placed in TBST (which may be supplied with the kit as discussed above). The samples may then be blocked with appropriate blocking reagents which may be supplied with the kit and used as described in Example 1. Suitable blocking agents include FC Receptor Block (bottle 15A, component 6) to block endogenous FC receptors; $H_2O_2$ to block endogenous peroxidases (bottle 15B, component 6) and biotin/avidin block complexes (bottle 15C for avidin and bottle 15D for biotin, component 6)

The samples are then incubated with primary antibody as described in Example 2. Any antibody specific for HCMV may be used. Suitable antibodies include, but are not limited to, those specific for IE1/IE2, (bottle 7) a cocktail of CMV antigens (bottle 8) and the CMV Late Ag (bottle 9). The primary antibodies are supplied in separate containers (component 4, bottles 7-9) and are used at the dilutions specified by the kit as described in Example 2. A solution (bottle 9) for antibody dilution may also be supplied such as Common Antibody Diluent, Biogenix Laboratories. Isotype matched negative control primary antibodies (Cd34 bottle, 20 and smooth muscle actin, bottle 21) are also utilized as well as positive control tissue (bottle 6). The positive control tissue may be premounted on an appropriate slide. The samples are washed in TBST to remove unbound primary antibody. The samples are incubated with secondary antibodies and appropriate signal generating reagents as described in Example 2. The secondary antibodies may be supplied with the kit in bottle 10 and used at the dilution specified. The samples are washed with TBST to remove unbound secondary antibody. Appropriate reporter groups are added to bind to the secondary antibodies. The reporter groups may be supplied in bottle 11 and used at the dilution specified. Appropriate detection substrates may then be added for visualization (bottle 16) along with chromogen enhancer, if desired (bottle 17). The samples may then be counterstained and mounted using the reagents in bottles 18-20 as described in Example 2.

The above example illustrates one embodiment of a kit for use in detecting HCMV by immunohistochemical means. The kit may be varied to incorporate features of the assay described in the immunohistochemistry section above as would be obvious to one of ordinary skill in the art provided with the teachings of this disclosure. Furthermore, not all of the components described above need be incorporated with the kit and additional components may be added. The kit may also contain detailed instructions for use to enable a user to complete the assay envisioned by the kit with no undue experimentation.

All references to articles, books, patents, websites and other publications in this disclosure are considered incorporated by reference.

TABLE 1

Detection of HCMV proteins in different grade gliomas, meningiomas, other CNS diseases, and normal brain. Anti-IE1-72 antibody was reactive with HCMV positive control tissues and non-reactive with HSV-1 infected tissue.

| Specimen | mAb specific for IEI-72 | pp65 | IE/EA | p52/76kD CD34 |
|---|---|---|---|---|
| Glioblastoma | 22/22 | 8/8 | 8/8 | 0/22 |
| Grade III oligo-Astrocytoma | 1/1 | | | 0/1 |
| Grade II Astrocytoma | 4/4 | 2/2 | 2/2 | 0/4 |
| Normal Brain | 0/5 | 0/1 | | 0/5 |
| Meningioma | 0/9 | | | |
| Stroke | 0/4 | | | |
| Alzheimer's | 0/3 | | | |
| Paraneoplastic Encephalitis | 0/1 | | | |
| Cryptococcal cerebriis | 0/1 | | | |

TABLE 2

Detection of HCMV nucleic acid in different grade gliomas, meningiomas, other CNS diseases, and normal brain.

| Specimen | Biotinylated oligo probe Specified for: HCMV RNA | HSV-1/2 RNA | HCMV digoxigenin labeled total genome DNA probe HCMV |
|---|---|---|---|
| Glioblastoma | 8/8 | 0/3 | 4/4 |
| Grade II Astrocytoma | 2/2 | 0/2 | 2/2 |
| Normal Brain | 0/4 | 0/3 | 0/4 |
| Meningioma | 0/5 | | |
| Stroke | 0/1 | | |
| Alzheimer's | 0/2 | | |
| Paraneoplastic Encephalitis | 0/1 | | |
| Cryptococcal cerebriis | 0/1 | | |

TABLE 3

Detection of HCMV proteins in human prostate adenocarcinomas and prostatic intraepithelial neoplasia (PIN) lesions.

| Sample | IHC IE1-72 | Pp65 | −C | PCR UL73 |
|---|---|---|---|---|
| 1 | + | | − | |
| 2 | + | + | − | + |
| 3 | + | | − | |
| 4 | + | | − | |
| 5 | + | | − | |
| 6 | + | | − | |
| 7 | + | | − | |
| 8 | + | | − | |
| 9 | + | | − | |
| 10 | + | + | − | + |
| 11 | + | + | − | |
| 12 | + | | − | |
| 13 | + | + | − | |
| 14 | − | + | − | |
| 15 | + | + | − | + |
| 16 | + | | − | |
| 17 | + | | − | + |
| 18 | + | | − | |
| 19 | + | | − | |

TABLE 4

Detection of HCMV nucleic acid in different grade colorectal polyps and adenocarcinoma (nnc = nonneoplastic colonic epithelium; p = polyp; ac = adenocarcinoma). Asterisk indicates that immunoreactivity was present only in blood vessels.

| Pt. # | Specimen | IE1 | pp65 | COX-2 | CD-34* | HCMV mRNA in situ IE/−c/HSV/Poly-T | UL55 PCR |
|---|---|---|---|---|---|---|---|
| 1 | nnc | − | − | | − | | |
| 2 | nnc | − | | | − | | − |
| | p | + | + | + | − | | |
| | ac | + | + | | | | + |
| 3 | p | + | | + | − | +/−/ /+ | |
| 4 | p | + | + | + | − | +/−/−/+ | |
| 5 | ac | + | + | | − | | |
| 6 | p | + | + | | | | + |
| 7 | p | + | | | − | | |
| 8 | nnc | − | | | − | | |
| | p | + | + | | | | |
| 9 | p | + | + | + | | +/ /−/ | |
| 10 | p | + | | | | | |
| 11 | p | − | | | − | | |
| 12 | p | + | + | | | | |
| 13 | p | + | | + | − | +/−/−/+ | |
| 14 | p | + | + | + | − | +/−/ /+ | |
| 15 | p | − | | | − | | |
| 16 | p | + | | | | + | |
| | p | + | | | − | | |
| | ac | + | + | | | + | |
| 17 | ac | + | + | + | − | + | |
| 18 | ac | − | | + | − | +/−/ /+ | |
| 19 | ac | + | | | − | + | |
| 20 | ac | + | + | + | − | + | + |
| 21 | ac | + | + | | | + | |
| 22 | ac | + | + | | − | | |
| | nnc | − | | | | | |
| 23 | ac | + | + | + | − | +/−/−/+ | |
| | nnc | − | | | − | | |
| 24 | ac | + | + | + | − | +/−/ /+ | + |
| | nnc | | | − | | − | |
| | nnc | − | | | − | | |
| 25 | p | − | − | | | | |
| | ac | + | + | + | − | +/ / /+ | |
| 26 | nnc | − | − | | − | | |
| | ac | − | | | | | |
| 27 | p | + | − | | − | | |
| | ac | + | + | | − | +/ / /+ | + |
| 28 | ac | − | − | | | | |
| 29 | ac | | | | | + | |
| | nnc | | | | | − | |

TABLE 5

Exemplary ranges for thickness of paraffin slices to be used in the immunohistochemistry and in situ hybridization assays described above.

| TISSUE TYPE | THICKNESS |
|---|---|
| BREAST | 4 microns |
| PROSTATE | 4-5 microns |
| COLON | 4-5 microns |
| OVARY | 4 microns |
| CERVIX | 4 microns |

TABLE 6

Exemplary conditions for various tissue types to be used in the immunohistochemistry and in situ hybridization assays described above.

| TISSUE TYPE | ANTIBODY | ENZYME | BLOCKING CONDITION |
|---|---|---|---|
| BRAIN TUMOR | CMV-IE | Pepsin | Avidin, FC |
| | CMV Late Ag | Pepsin | Avidin, FC |

TABLE 6-continued

Exemplary conditions for various tissue types to be used in the immunohistochemistry and in situ hybridization assays described above.

| TISSUE TYPE | ANTIBODY | ENZYME | BLOCKING CONDITION |
|---|---|---|---|
| BREAST | IE1, IE2 | Pepsin | Avidin, FC |
|  | PP65 | Trypsin or Pepsin | Avidin, FC |
|  | Cocktail | Trypsin | Avidin, FC |
| COLON | IE, IE1 | Pepsin | FC |
|  | IE2 | Pepsin | Avidin, FC |
|  | Cocktail | Pepsin | BB |
|  | PP65 | Trypsin | FC |
| PROSTATE | IE1. IE2, PP65 | Pepsin | FC |
|  | Cocktail | Pepsin | BB |
| Ovary | IE1 | Pepsin | FC |
|  | Cocktail | Pepsin | BB |
|  | IE2, PP65 | Pepsin | Avidin, FC |
| Cervix | IE1, IE2, PP65 | Pepsin | FC |
|  | Cocktail | Pepsin | BB |

TABLE 7

Exemplary antibody dilutions to be used in the immunohistochemistry and in situ hybridization assays described above.

| ANTIBODY | ANTIBODY TYPE | SOURCE | DILLUTION |
|---|---|---|---|
| CMV COCKTAI | Monoclonal | Innovex Biosciences ® | 1:50-1:70 |
| CMV Late Ag | Monoclonal | Chemicon ® | 1:25-1:35 |
| PP65 | Monoclonal | Novocastra ® | 1:35-1:45 |
| CMV IE | Monoclonal | Biogenex ® | 1:15-1:25 |

What is claimed:

1. A method for detecting the presence of an HCMV in a cancer tissue sample, the method comprising the steps of:
   a) providing said cancer tissue sample suspected of containing HCMV from a subject, said tissue sample being embedded in a paraffin matrix, sectioning said tissue sample to a thickness of 3, 4, 5, 6, or 7 microns, and then mounting said tissue sample to a transparent support;
   b) subjecting said tissue sample to a de-paraffinizing procedure comprising rinsing said tissue sample in xylene at least one time, followed by rinsing said tissue sample at least one time in a series of ethanol solutions of decreasing concentration, said decreasing ethanol concentrations are selected from the group consisting of 100%, 95%, 75% and 50%;
   c) subjecting said tissue sample to an epitope condition procedure to reduce epitope variability in said tissue sample comprising incubating said tissue sample in 10% neutral buffered formalin for a time period sufficient for epitope conditioning and subjecting said tissue samples to digestion with an enzyme;
   d) subjecting said tissue sample to an antigen retrieval procedure comprising incubating said tissue sample in a citra buffer if the tissue samples were originally fixed with a formalin based fixative or in a distilled water if the tissue samples were originally fixed in a non-formalin based fixative for a time period sufficient for said antigen retrieval;
   e) contacting the tissue sample with a blocking agent selected from the group consisting of:
      (i) an agent that blocks endogenous peroxides and an agent that blocks FC receptors;
      (ii) an avidin agent and an agent that blocks FC receptors;
      (iii) an avidin agent, an agent that blocks FC receptors and an agent that blocks endogenous peroxides; and
      (iv) an agent that blocks FC receptors;
   (f) contacting said tissue sample with at least one antibody capable of binding to at least one epitope of HCMV to form an antibody-epitope complex, under conditions suitable for binding of said antibody with said epitope; and
   (g) detecting said antibody epitope complex.

2. The method of claim 1, wherein the tissue is obtained from a glial, a breast, a prostate, a colon, a cervical or an ovarian tissue.

3. The method of claim 1, wherein the tissue sample is obtained from glial tissue and the paraffin matrix has a thickness of 6 microns.

4. The method of claim 1, wherein the tissue sample is obtained from breast, prostate, colon, cervical or ovarian tissue and the paraffin matrix has a thickness of 4 microns or 5 microns.

5. The method of claim 1, wherein the time period sufficient for epitope conditioning is determined by the age of the tissue sample.

6. The method of claim 5, wherein the time period is selected from the group consisting of: 15 to 20 minutes for tissue sample less than 30 days old; 45 to 60 minutes for tissue samples 2 to 6 months old; 90 to 1800 minutes for tissue samples 6 to 24 months old; 180 to 240 minutes for tissue samples 24 to 48 months old; and 240 to 360 minutes for tissue samples over 48 months old.

7. The method of claim 1, wherein the enzyme is a pepsin or a trypsin and the digestion occurs at 37° C. for 4 to 6 minutes.

8. The method of claim 1, wherein the time period of (d) is about 2 to 2.5 hours.

9. The method of claim 8, wherein the incubation of said tissue sample with said citra buffer is takes place in a water bath having a temperature of 45-50° C. and said citra buffer is pre-warmed to a range of 85-90° C. and has a pH of 7.6.

10. The method of claim 1 further comprising incubating said tissue sample in at least one blocking reagent selected from the group consisting of a hydrogen peroxide solution, an avidin/biotin solution and a protein blocking solution.

11. The method of claim 1, wherein the at least one antibody is directed against at least one protein selected from the group consisting of IE1, IE2, pp65, or CMV late antigen.

12. The method of claim 11, wherein the antibodies are diluted in a buffer and used within 24 hours after dilution.

13. The method of claim 11, wherein the antibodies are incubated with said tissue sample at 4-8° C. overnight in a humidified container.

14. The method of claim 1, wherein the detecting step comprises incubation of the antigen-epitope complex with a secondary antibody and a signal producing reagent, said signal producing reagent comprising a least one of a labeling reagent capable of interacting with the secondary antibody, a chromogen capable of transformation by the labeling reagent to a detectable signal and a chromogen enhancer.

15. The method of claim 1, wherein the tissue samples are washed with a washing solution between the steps of the method of claim 1, said washing solution being TBS, TBST or water.

16. The method of claim 1, wherein the detection is specific for a specific strain of HCMV.

17. The method of claim 16, wherein the specific strain of HCMV is HDu.

18. The method of claim 16, wherein the specific strain of HCMV is HDu and where the detection is specific for glycoprotein N.

19. A method of determining if a human subject has a cancer comprising an HCMV infection, said method comprising the steps of:
   a) providing a tissue sample suspected of containing HCMV from said subject having a cancer;
   b) determining if HCMV is present in said tissue sample, comprising:
      (i) embedding the tissue sample in a paraffin matrix, sectioning said tissue sample to a thickness of 3, 4, 5, 6, or 7 microns, and then mounting said tissue sample to a transparent support;
      (ii) subjecting said tissue sample to a de-paraffinizing procedure comprising rinsing said tissue sample in xylene at least one time, followed by rinsing said tissue sample at least one time in a series of ethanol solutions of decreasing concentration, said decreasing ethanol concentrations are selected from the group consisting of 100%, 95%, 75% and 50%;

(iii) subjecting said tissue sample to an epitope condition procedure to reduce epitope variability in said tissue sample comprising incubating said tissue sample in 10% neutral buffered formalin for a time period sufficient for epitope conditioning and subjecting said tissue samples to digestion with an enzyme;

(iv) subjecting said tissue sample to an antigen retrieval procedure comprising incubating said tissue sample in a citra buffer if the tissue samples were originally fixed with a formalin based fixative or in a distilled water if the tissue samples were originally fixed in a non-formalin based fixative for a time period sufficient for said antigen retrieval;

(v) contacting the tissue sample with a blocking agent selected from the group consisting of:
  (A) an agent that blocks endogenous peroxides and an agent that blocks FC receptors;
  (B) an avidin agent and an agent that blocks FC receptors;
  (C) an avidin agent, an agent that blocks FC receptors and an agent that blocks endogenous peroxides; and
  (D) an agent that blocks FC receptors;

(vi) contacting said tissue sample with at least one antibody capable of binding to at least one epitope of HCMV to form an antibody-epitope complex, under conditions suitable for binding of said antibody with said epitope;

c) detecting said antibody epitope complex; and
d) providing an indication of an HCMV in the cancer to a clinician.

20. The method of claim 19, wherein said determining is specific for a specific strain of HMCV.

21. The method of claim 20, wherein the specific strain of HCMV is HDu.

22. The method of claim 20, wherein the specific strain of HCMV is HDu and where the determining is specific for glycoprotein N.

23. The method of claim 19, further comprising providing a negative control tissue and determining whether a level of HCMV in said tissue sample is greater than a level of HCMV in said negative control tissue sample.

24. The method of claim 19, wherein the cancer is selected from the group consisting of glioma, breast cancer, prostate cancer, colon cancer, cervical cancer or ovarian cancer.

25. The method of claim 19, wherein the tissue sample is obtained from a glial, a breast, a prostate, a colon, a cervical or an ovarian tissue.

26. The method of claim 1, wherein the at least one antibody comprises an anti-IE1-72 antibody.

27. The method of claim 19, wherein the at least one antibody comprises an anti-IE1-72 antibody.

28. The method of claim 26, wherein the anti-IE1-72 antibody is a monoclonal antibody.

29. The method of claim 27, wherein the anti-IE1-72 antibody is a monoclonal antibody.

* * * * *